(12) United States Patent
Hang et al.

(10) Patent No.: US 6,399,936 B1
(45) Date of Patent: *Jun. 4, 2002

(54) OPTICAL CONFOCAL DEVICE HAVING A COMMON LIGHT DIRECTING MEANS

(75) Inventors: Zhijiang Hang, Lexington; Victor Lazarev, Burlington; Robert H. Webb, Lincoln, all of MA (US)

(73) Assignee: New Dimension Research Instrument, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/407,458

(22) Filed: Sep. 28, 1999

Related U.S. Application Data

(63) Continuation-in-part of application No. 08/982,103, filed on Dec. 1, 1997.

(51) Int. Cl.$^7$ .................................................. H01J 3/14
(52) U.S. Cl. ...................... 250/216; 250/208.1; 257/82
(58) Field of Search .............................. 250/216, 201.3, 250/208.1, 208.2, 234, 553; 257/80–84; 359/27

(56) References Cited

U.S. PATENT DOCUMENTS

| | | | | |
|---|---|---|---|---|
| 3,819,938 A | * | 6/1974 | Kornrumpf et al. | 250/222.1 |
| 4,988,153 A | * | 1/1991 | Paek | 359/15 |
| 5,028,802 A | * | 7/1991 | Webb et al. | 250/235 |
| 5,563,710 A | * | 10/1996 | Webb et al. | 356/445 |
| 6,121,603 A | * | 9/2000 | Hang et al. | 250/216 |

* cited by examiner

Primary Examiner—Que T. Le
Assistant Examiner—Thanh X. Luu
(74) Attorney, Agent, or Firm—O'Connell Law Firm

(57) ABSTRACT

A confocal scanning imaging device for viewing an object includes an array of independently addressable microlasers and an array of detectors for detecting light from an object to which light from the microlasers has been directed. The array of microlasers and the array of detectors are combined into a single array, such as on a single chip, and in a pattern constructed and arranged so that different detectors are adjacent to each microlaser so that light from an illuminated object may be directed back to the vicinity of the illuminating microlaser and be detected by the adjacent detector(s). An optical arrangement directs light generated by the microlasers onto an object and directs light from an object so illuminated onto detectors adjacent to the illuminating microlaser. The optical arrangement includes a bilens and a matching lens system including two objective lenses. A microlens of pitch substantially identical to the pitch of the microlaser array collimates light generated by the microlasers. The system is constructed so that the relationships are as follows:

$$\Delta = \delta_1 f_1 / f_2$$

$$\delta_2 = \delta_1 f_3 / f_1$$

where $\Delta$ is the distance between the optical centers of the bilens, $\delta_2$ is the distance between sequentially illuminated points on the object, $\delta_1$ is the distance between neighboring elements in the array, the focal length of the bilens is $f_2$ and the focal length of the objective lens nearest the array is $f_1$, and the focal length of the objective lens furthest from the array is $f_3$.

31 Claims, 14 Drawing Sheets

OPTICAL CONFOCAL DEVICE HAVING A COMMON LIGHT DIRECTING MEANS

This application is a continuation-in-part of copending application Ser. No. 08/982,103 filed on Dec. 1, 1997.

FIELD OF THE INVENTION

The invention disclosed herein relates generally to optical instruments and methods. Stated more particularly, disclosed and protected by the present patent is a scanning confocal device for scanning an object with an optical beam, detecting the light remitted from or reflected by the object, and generating an image of the object.

BACKGROUND OF THE INVENTION

Confocal imaging techniques include the illumination of objects with a "flying spot" and the detection of light that is reflected from or otherwise remitted by the currently illuminated point on the object located only in the image plane. This provides better spatial resolution, better contrast to the image, and less depth of field than conventional optical devices. The small depth of field allows for the creation of 3-D images of semi-transparent objects. Scanning imaging techniques are employed in confocal laser scanning microscopes (CLSM), tandem scanning microscopes (TSM), scanning laser ophthalmoscopes (SLO), and other applications.

A TSM is discussed in Petran et al., "Tandem-Scanning Reflected-Light Microscope," *Journal of the Optical Society of America* 1968 Vol. 58, No. 5, pp 661–664. Petran et al. acknowledged that reflected-light microscopy of semi-transparent material is usually unsatisfactory because of low contrast and light scattering. They describe the TSM, in which both the object plane and the image plane are scanned in tandem. In the Petran et al. system, the object is illuminated with light passing through holes in one sector or side of a rotating scanning disk, known as a Nipkow disk. The scanning disk is imaged by the objective at the object plane. Reflected-light images of these spots thereby produced are directed to the diametrically opposite side of the same disk. With this, light can pass from the source to the object plane, and, from the object plane to the image plane, only through optically congruent holes on diametrically opposite sides of the rotating disk.

Tandem scanning confocal arrangements, however, are "light-starved" by the limited brightness of the illumination spot. TSM systems, in addition, are hampered by stray light scattered from the moving pinhole array.

Current flying spot systems benefit from the advent of the laser. They use moving optical elements for deflecting a laser beam, so that an illumination spot is swept across the object to be scanned.

A recent version of a CLSM is described in U.S. Pat. No. 5,532,873 of Dixon. The scanning of the laser beam is provided by two mirrors, rotationally oscillating around axes that are perpendicular to each other.

A confocal scanning laser ophthalmoscope (CSLO) is disclosed in Webb et al, "Confocal Scanning Laser Ophthalmoscope," *Applied Optics,* Vol. 26, No. 8, Apr. 15, 1987, pp 1492–1499. The apparatus uses multiple scanning elements, including a multifaceted rotating polygonal reflector scanner, to provide scanning of both incident and reflected light at television-rate frequencies. The CSLO scans an illumination spot over the fundus of an eye, and synchronously scans a detector over the image.

Other confocal devices, are discussed *in The Handbook of Biological Confocal Microscopy,* 2nd edition. Pawley, ed., Plenum Press, 1995.

Conventional scanning devices of the type discussed require a multiplicity of mechanical components moving at high speed. They are typically bulky and require significant power to drive the scanning mechanism.

A confocal scanning device without moving parts is described in U.S. Pat. No. 5,028,802 of Webb et al,. FIG. 1A of the present application (which is FIG. 1C of the '802 patent) provides a summary of the Webb et al. invention and is prior art. FIG. 1B of the present application (FIG. 3 of the '802 patent) shows the preferred embodiment of the '802 patent.

Referring to FIG. 1C of the '802 patent (FIG. 1A of the present application), the scanning arrangement employs N×M array 10 of microlasers in a scanning mode as the illumination source. As shown in FIG. 1A of the present application (FIG. 1C of Webb), the device includes a laser scan drive 16 for energizing the lasers of array 10. The microlasers are energized sequentially, so that the array 10 is scanned in a conventional TV raster fashion. The array 10 is imaged on the object 18 to be illuminated thereby providing raster illumination of the object 18. Light 19 emitted from the object, by reflection, scatter or transmission, is then detected by detector 20 and the detection signal, carried on line 21, is displayed synchronously with the array scan, to provide a video image on a monitor or other image output device 22 driven by SYNCH signals provided by drive 16 on line 24.

Referring to FIG. 1B of the present application (FIG. 3 of Webb), a confocal scanning configuration uses a detector array having independently addressable photodiodes, that are optically congruent to microlasers. Lens L directs light from scanned source array 10 onto the object plane OB, and light reflected from the object is directed to detector 20 by beam splitter S. A lens L' is used to direct light reflected from the object onto discrete photodiodes of a detector array 20'. These photodiodes are read individually, in a pattern that is, and are synchronized with the scanning-illumination of the object. Thus, light scattered from non-illuminated portions of the object does not contribute to the output of the detection device, unless it impinges upon the selected portion of the detector. As a result, noise due to unwanted scattered light is significantly reduced.

U.S. Pat. No. 5,034,613 to Denk et al., which issued Jul. 23, 1991 for Two-Photon Laser Microscopy, discloses a laser scanning microscope in which fluorescent light is detected in a manner intended to avoid photo-bleaching.

U.S. Pat. No. 5,071,246 to Blaha et al., which issued Dec. 10, 1991 for Confocal Scanning Ophthalmoscope, discloses the use of light wave conductors.

U.S. Pat. No. 5,120,953 to Harris, which issued Jun. 9, 1992 for Scanning Confocal Microscope Including A Single Fiber For Transmitting Light To and Receiving Light From An Object, discloses the use of optical fibers for transmitting light and a light separator to divert the return light to a detector.

U.S. Pat. No. 5,296,703 to Tsien, which issued Mar. 22, 1994 for Scanning Confocal Microscope Using Fluorescence Detection, discloses the use of a beam of radiation and detection of the resulting fluorescence using beam splitters and rotatable scanning mirrors and a raster scan display.

U.S. Pat. No. 5,325,386 to Jewell et al., which issued Jun. 28, 1994 for Vertical-Cavity Surface Emitting Laser Array Display System, discloses the use of vertical cavity surface emitting lasers in an array to enhance a display.

U.S. Pat. No. 5,386,112 to Dixon, which issued Jan. 31, 1995 for Apparatus and Method for Transmitted-Light and Reflected-Light Imaging, discloses a microscope using a series of beam splitters and mirrors and light that is reflected is separated from light that is transmitted.

U.S. Pat. No. 5,430,509 to Kobayashi, which issued Jul. 4, 1995 for Scanning Laser Ophthalmoscope, discloses the use of beam splitters and mirrors and uses at least three scanning systems.

U.S. Pat. No. 5,450,501 to Smid issued Sep. 12, 1995 and is directed to an Apparatus for the Point-by-Point Scanning of an Object using frequency selective filtration to operate a system having transmission of light through the object being viewed.

U.S. Pat. No. 5,512,749 to Iddan et al., which issued Apr. 30, 1996 for Infrared Microscope, discloses the use of a cryogenic detection device and an IR array of detectors including a scanning mirror for scanning the object.

U.S. Pat. No. 5,524,479 to Harp et al. issued Jun. 11, 1996 and is directed to a Detecting System for Scanning Microscopes. The patent discloses the use of a cantilevered arm as a probe to examine the object to be viewed.

U.S. Pat. No. 5,563,710 to Webb, which issued Oct. 8, 1996 for Imaging System With Confocally Self-Detecting Laser, discloses using an array of lasers and a single detector. Also, light reflected from the object effects the lasers, which then forward the light to the detector.

U.S. Pat. No. 5,568,463 to Sahara et al. issued Oct. 22, 1996 and discloses a Semiconductor Laser Device To detect A Divided Reflected Light Beam. The patent describes an optical device for detecting a magneto-optical signal in which a light-emitting portion and a light receiving portion are closely disposed on a common substrate.

BRIEF SUMMARY OF THE INVENTION

A general object of the present invention is to provide improved confocal imaging methods and apparatus without the use of moving parts.

A further object of the present invention is to provide such methods and apparatus affording high spatial resolution and enhanced brightness of the image.

Another object of the present invention is to provide such imaging methods and apparatus that is capable of being implemented in a compact and reliable embodiment.

A further object of the present invention is to provide a confocal scanning device that is arranged so that multiple areas of a target may be scanned simultaneously.

Another object of the present invention is to provide a small angle beam splitter (SABS) in a confocal arrangement that permits extremely small angle shifts for light beams.

A further object of the present invention is to provide a device of the type described that is arranged to be used as a microscope.

An additional object of the present invention is to provide a device of the type described that is arranged to be used as an Ophthalmoscope.

A yet further object of the present invention is to provide a confocal device and method that can be accomplished using light fiber bundles, both of the coherent and the non-coherent type.

Still another object of the present invention is to provide for the imaging of an object in fluorescent light.

Yet another object of the present invention is to provide a two-photon confocal device that is versatile and compact.

A further object of the present invention is to provide for complete utilization of light emitted by microlasers thereby to increase the brightness of the image.

These and still further objects and advantages of the present invention will be obvious both to one who reviews the present description and the accompanying drawings and to one who has an opportunity to take advantage of an embodiment of the present invention for an optical confocal device.

In furtherance of these objects, one embodiment of the invention includes a combined array of independently excitable light sources and independently readable detectors that are supplemented by optical elements for directing the light generated by the light sources of the array onto the object and for directing light that is reflected, fluoresced or scattered from the object onto the detectors of the array. There may be rows of light sources and detectors that are interleaved in a combined array. The source/detector array and optical elements can be, and preferably are, stationary relative to one another and relative to the object.

A small angle beam splitter is provided to deflect the reflected and remitted light from the object to the detectors. Since the spacing between adjacent microlasers and detectors is quite small, a bilens is used to provide this shift. The requirement imposed upon such a bilens for there to be some difference (e.g., $5\mu$) between the lenses causes such a bilens to be difficult at best to make. Therefore, an optical system is used wherein the requirements imposed on the bilens can be more in the order of one mm rather than 5 $\mu$m. If the spacing between adjacent lasers and detectors is in the range of 10–90$\mu$, then the difference in the bilens would be in the range of 5–45$\mu$ since the difference in the bilens is one half of the spacing of laser to detector.

Each embodiment according to the present invention can be used for the imaging of an object in fluorescent light. The fluorescence technique is used both in an ophthalmoscope for the imaging of a blood vessel picture of the retina and in various applications of microscopy, especially when it is desired to obtain a 3-D view of tissue. It provides high sensitivity to the presence of small amounts of fluorescent substances. The laser scanning technique produces excitation in a target material by absorption of photons thereby to provide intrinsic three-dimensional resolution. The confocal technique additionally brings better image contrast and the opportunity for 3-D fluorescent imaging.

The combined laser/detector array can be arranged for the simultaneous excitation of several spaced light sources that are reflected or otherwise returned to the array where they are detected as long as the direct or reflected, refracted or fluoresced light from the different light sources does not adversely influence any of the other simultaneously excited light sources/detectors combinations. This can provide a several-fold increase in the speed of scanning an object with a confocal device.

The foregoing discussion broadly outlines the more important features of the invention to enable a better understanding of the detailed description that follows and to instill a better appreciation of the inventors' contribution to the art. Before an embodiment of the invention is explained in detail, it must be made clear that the following details of construction, descriptions of geometry, and illustrations of inventive concepts are mere examples of the many possible manifestations of the invention.

DETAILED DESCRIPTION OF PREFERRED EMBODIMENTS

As is the case with many inventions, the present invention for an optical confocal device is subject to a wide variety of embodiments. However, to ensure that one skilled in the art will fully understand and, in appropriate cases, be able to practice the present invention, certain preferred embodiments of the broader invention revealed herein are described below and shown in the accompanying drawings.

Figure 2A:
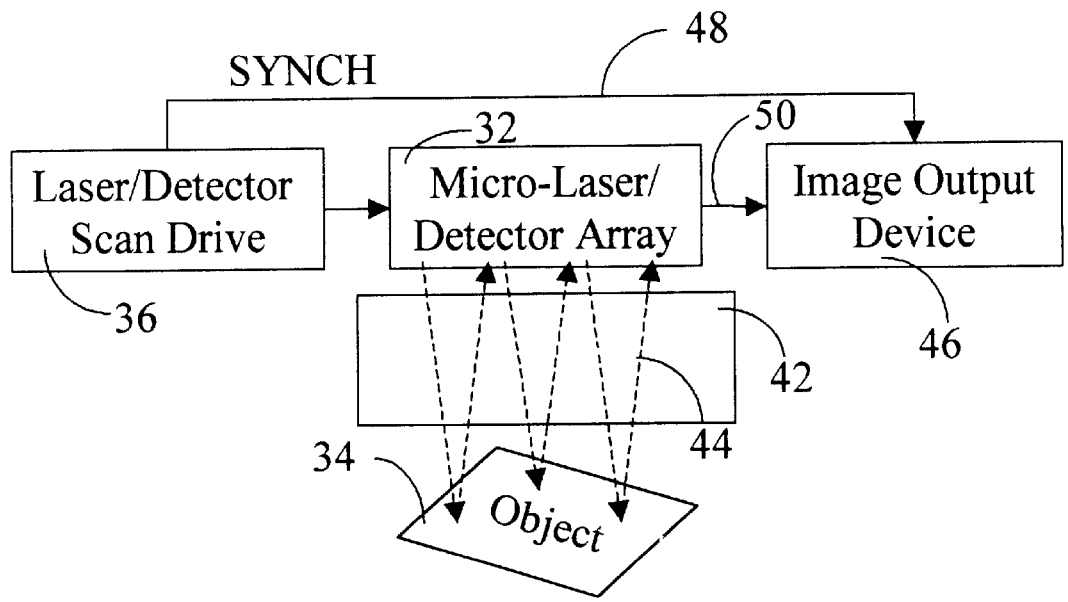
FIG. 2A is a diagrammatic block diagram of a scannable microlaser device according to the present invention.
Figure 2B:
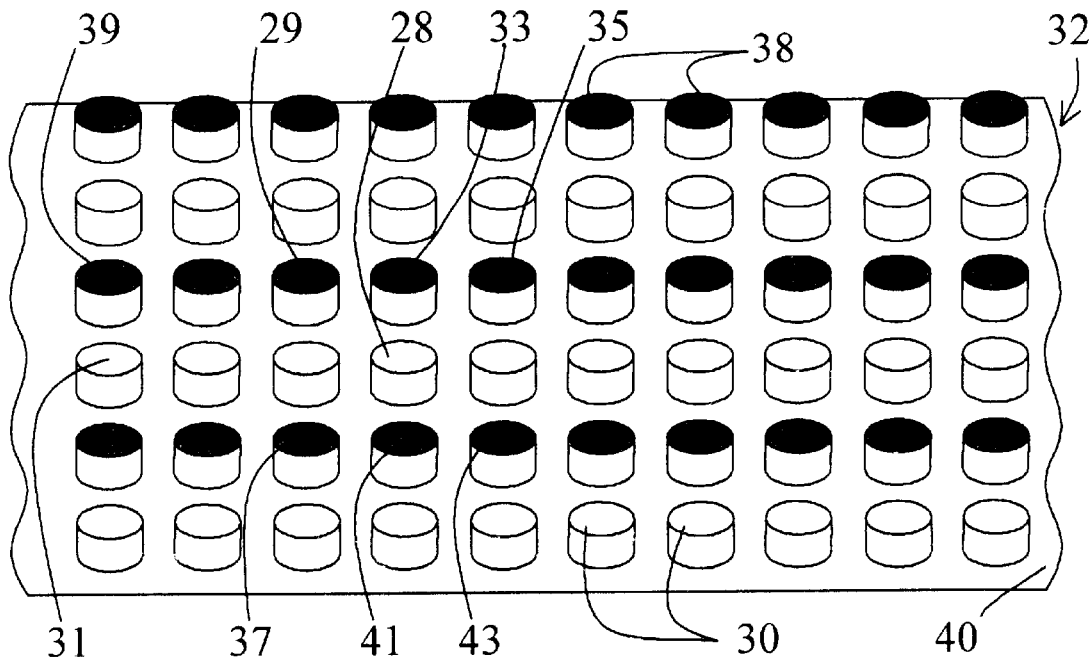
FIG. 2B is a schematic diagram of a combined array of microlasers and detectors.

The Broad Concept—FIGS. 2A and 2B

Figure 1A:
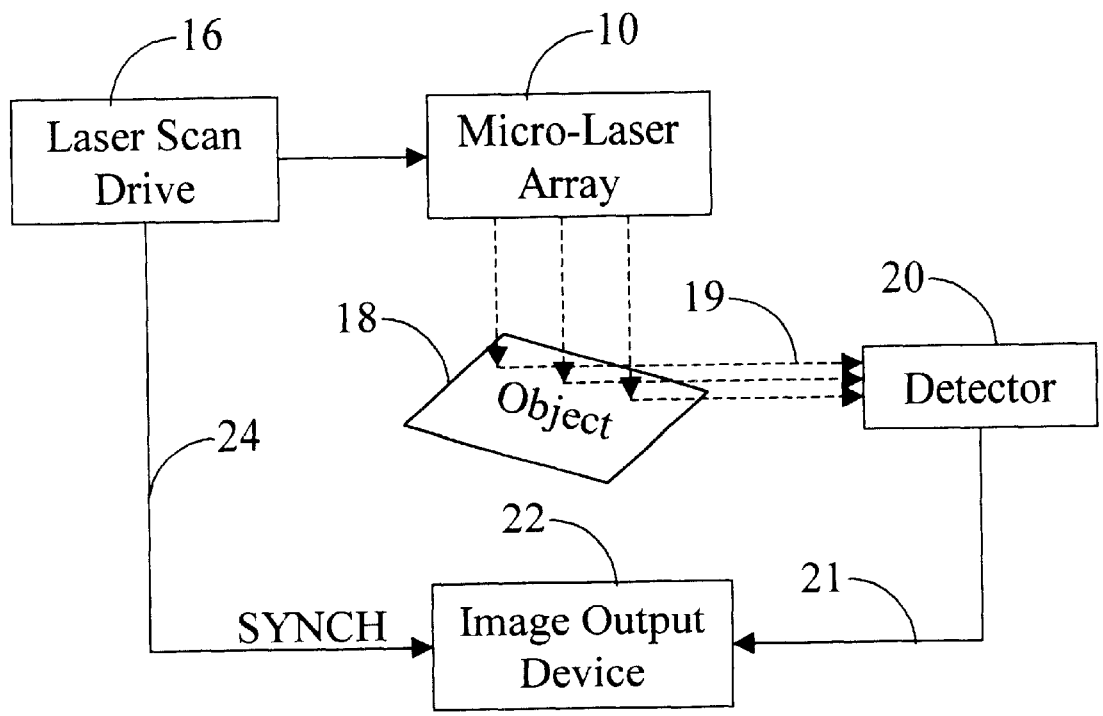
FIG. 1A is a diagrammatic block diagram of the prior art as shown in U.S. Pat. No. 5,532,873.

The present invention provides confocal scanning imaging methods and apparatus, as shown in FIGS. 2A and 2B, that employ an array of microlasers 30 in a scanning mode as the illumination source, an array of detectors 38 in a scanning mode interleaved with the microlasers 30 on the same substrate 40, and an optical system 42 that provides the optical congruency of both arrays. The invention preferably includes a combined array 32 as shown in FIGS. 2A and 2B. A comparison of FIG. 2A (the invention) with FIG. 1A (the prior art) suggests the reduction in size for the device of the present invention. That is, the same size array as used only for the microlasers in the prior art is used for the combined arrays of microlasers 30 and detectors 38 in the present invention.

Referring to FIGS. 2A and 2B, microlasers 30 in a combined laser/detector array 32 are imaged on the object 34 to be illuminated to provide raster illumination of the object. The light 44, reflected from or scattered, or in some cases fluoresced, by the object 34, is directed to the same array 32, but slightly shifted to be projected onto detectors 38. The detection signal carried on line 50 is displayed synchronously with the array scan to provide a video image on a monitor or other image output device 46 driven by SYNCH signals provided by drive 36 on line 48. In FIG. 2B, as well as in the other figures, lasers 30 are marked with open circles while detectors 38 are marked with shaded circles or in solid black. Drive 36 provides the direction of scanning lines in the raster of sequentially activated lasers 30 and the reading of neighboring detectors 38 to be perpendicular to the interlaced lines of lasers 30 and detectors 38 in array 32.

Current microlasers have threshold currents as low as 250 $\mu A$, threshold voltages as low as 2V, 50% power conversion efficiency, and output powers as high as 15 mW [Choquette et al. "Threshold investigation of oxide-confined vertical cavity laser diodes." *Applied Physics Letters* 1996, Vol. 68, pp 3689–3691]. Among the variety of existing photodetectors, Resonance Cavity Photo Detectors (RCPD) are preferable to be included with VCSELs in the combined laser/detector array 32, which may alternatively be termed a laser/detector chip 32. Their quantum efficiency reaches as high as 85% [Ortiz et al "-Monolithic integration of $In_{0.2}Ga_{0.8}As$ vertical-cavity surface-emitting lasers with resonance-enhanced quantum well photodetectors", *Electronics Letters* 1996, Vol. 32, No 13, pp. 1205–1207]. Their structure can be realized by chemically removing some of the AlAs/AlGaAs quarter-wave layers from the top mirror of VCSEL's cavity. Therefore, the combined laser/detector chip 32 can be created from an array of VCSELS. Existing VCSEL arrays consist of microlasers with apertures of 10–25 $\mu m$, centered at 25–40 $\mu m$.

A laser and detector array 32 with control integrated-circuits can be bound together as a single chip 32 by so-called flip-bounding technique.

More Details of The Concept—FIGS. 3A, 3B, 3C and 3D

The small distance between neighboring lasers 30 and detectors 38 in a combined array 32 requires the presence of a Small Angle Beam Splitter (SABS) in the optical system of the device. The distinction in operation of such a system versus that of conventional beam splitters (FIG. 1B) is shown in FIGS. 3A, 3B and 3C.

Figure 3A:
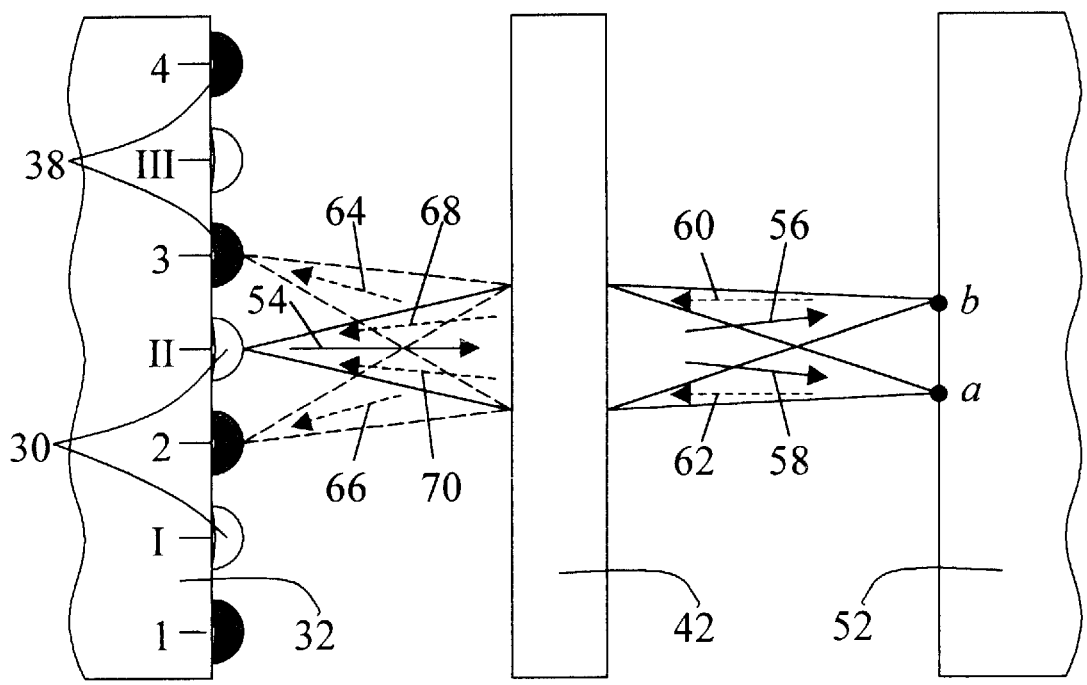
FIG. 3A is a diagrammatic view of a confocal scanning device embodying the present invention.

FIG. 3A shows the arrangement of microlaser/detector array 32, optical system 42, and object 52 and indicates the light patterns as transmitted and received.

Figure 3B:
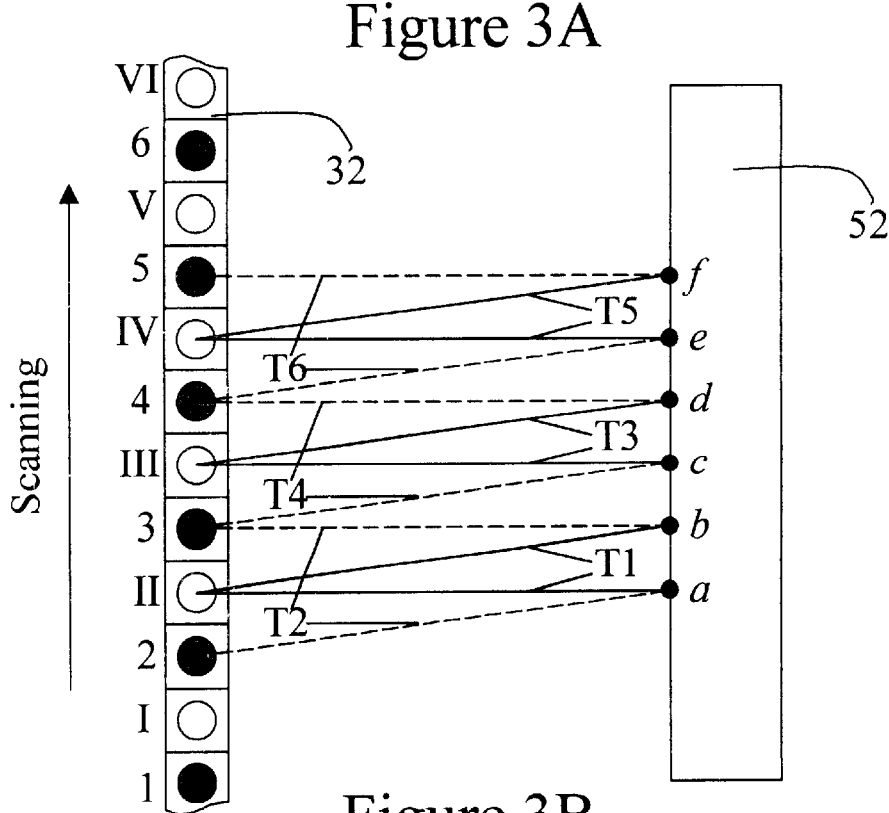
FIG. 3B is a schematic view showing the sequence of operation of the microlasers and detectors associated therewith, as well as points on the object that are illuminated.
Figure 3C:
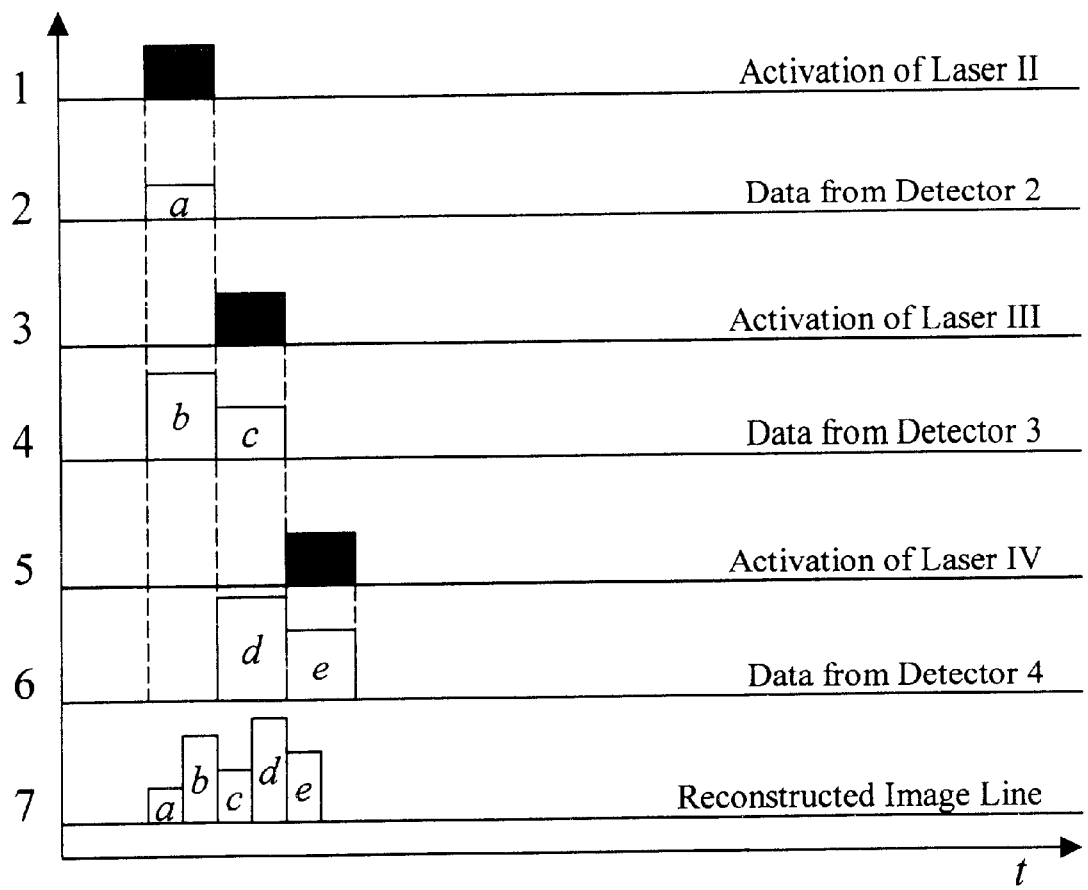
FIG. 3C is a graphical depiction of the time charts in the operation of the scanning microlaser device of FIGS. 3A and 3B.

FIG. 3B shows schematically the sequence of object illumination and of light detection during the scanning of the lasers. In FIG. 3B, the lasers are numbered with Roman digits, detectors are numbered with Arabic digits, and alpha-characters designate the sequentially illuminated points on the object 52. Solid lines join each laser and points on the object 52 illuminated from this laser. Dashed lines join illuminated points with corresponding detectors. The optical system is not shown in FIG. 3B since the lines shown therein are not light beams, but just indications of the directions and sequence of flow.

Thus, as shown in FIG. 3A, when microlaser "II" is activated (the sequence is the same for microlaser "I" except that the points on the object are slightly different and the detectors are slightly different) it produces light, the rays thereof being indicated by arrow 54, and the optical system 42 with the SABS produces two sets of rays of interest 56 and 58 which illuminate spots or points "b" and "a", respectively, on the object 52 from the currently operating laser 30 identified as "II". The light from each point "b" and "a" is reflected back as shown by arrows 60 and 62, respectively, to SABS 42 and is split again as shown by arrows 64, 66, 68 and 70. Part of the light, as shown by arrows 68 and 70 meets the array plane in initial position where the laser "II" is located. Another part of the light, as shown by arrows 64 and 66 is in shifted position with the detectors. Light designated by arrow 64 impinging upon detector "3" and light designated by arrow 66 impinging upon detector "2". The switching over to the next laser "III" in the array causes the illumination of the next pair of object points "c" and "d" and the light from these points impinges upon detectors "3" and "4".

FIGS. 3B and 3C show the sequence of laser and detector activation as well as time charts for laser and detector activation, as well as the method of image reconstruction from the data obtained from the detectors. FIG. 3B shows diagramatically the sequencing of the operation of the individual microlasers and detectors in the combined array. Looking at the second microlaser labeled "II" it is actuated at the first time point of interest and light is emitted and sent to points "a" and "b" as shown by sequence lines T1 indicating activation of microlaser "II" and impinging of light at points "a" and "b". In FIG. 3C this is shown on line 1 of the time chart. Light from points "a" and "b" is reflected back and some impinges on detector "2" (see line 2 of the time chart) and, at the same time, some impinges on detector "3" (see line 4 of the time chart). The latter sequence is shown by sequence lines T2 in FIG. 3B.

Next, microlaser "III" is activated as shown by line 3 of the time chart. This is shown by sequence lines T3 in FIG. 3B. Light from points "c" and "d" is reflected back and some impinges on detector "3" (see line 4 of the time chart) and, at the same time, some impinges on detector "4" (see line 6 of the time chart). The latter sequence is shown by sequence lines T4 in FIG. 3B. Next, microlaser "IV" is activated as shown by line 5 of the time chart. This is shown by sequence lines T5 in FIG. 3B. Light from points "e" and "f" is reflected back and some impinges on detector "4" (see line 6 of the time chart) as indicated by sequence lines T6. The process continues in this manner until the entire combined array has been used to provide light to the object and detect light from the object being viewed.

The section-lined rectangles in FIG. 3C are the time gates for the activation of the lasers. The height of the boxes with the characters indicates the intensity of the signal detected from corresponding points on the object. The ordered detectors data are saved in the frame memory buffer of the image output device 46 of FIG. 2A and will be displayed during the next frame, during which time the new data set is detected. Because of simultaneous detection of signals from two points on the object, the time interval of detection for each of them is two times the interval of its display. This is because spots "a" and "b" are illuminated at the same instant, but in the display, "b" must be after "a". This can be useful for the accumulation of signals to reduce the noise.

Figure 1B:
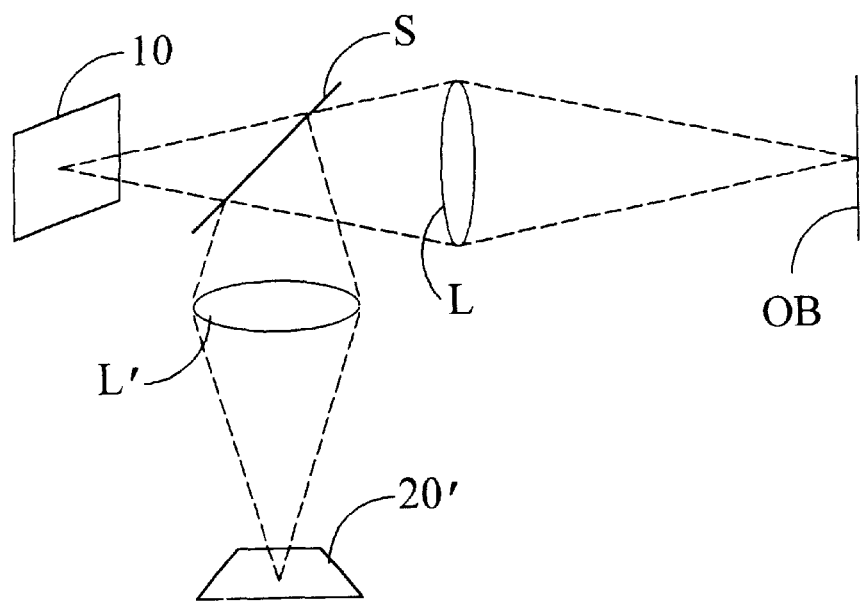
FIG. 1B is a diagrammatic view of a confocal scanning microscope of the prior art as shown in U.S. Pat. No. 5,532,873.

Therefore, the concept of the combined laser/detector array integrated with the concept of the SABS provides the design of confocal devices without moving parts with significant advantages. The SABS is required so that there is a shift of light by the distance from center to center between adjacent microlasers and detectors. This could be in the range of 25–40 µm. There are four points to be made concerning this construction:

First, the combination of two chips 10, 20' in FIG. 1B into only one chip 32 in FIG. 2A reduces the overall size of the device since a separate array of detectors in a different location than the microlaser array is no longer required.

Second, according to the arrangement shown in FIGS. 3A and 3B the spatial resolution of the image in this case depends on the total number of elements in the combined chip and not on the number of lasers or detectors separately. Therefore, the resolution is the same for both schematics (FIGS. 1A and 2A) if the integration level of the combined chip is equal to that of the laser or detector chip in FIG. 1B. This is because of the size and number. Even though there may be ½ as many detectors, since each detector is used for 2 points on the object, the same resolution is provided, e.g., detector "2" detects from point "b" and from point "c", whereas the previous arrangement only used one detector for one point on the object.

Third, the amount of light that is used for illumination of each point is the same for both types of arrangements although the light of each laser is divided into two parts in the version of the present invention. According to the version in FIG. 1B, half of the light from the laser is not used by the system because it is lost in the reflection from the beam splitter S.

Fourth, the time interval for the detection of light from each point on the object for the combined chip is twice as long as explained above in connection with FIGS. 3A, 3B and 3C, and this can reduce noise due to accumulation of signals.

Figure 4A:
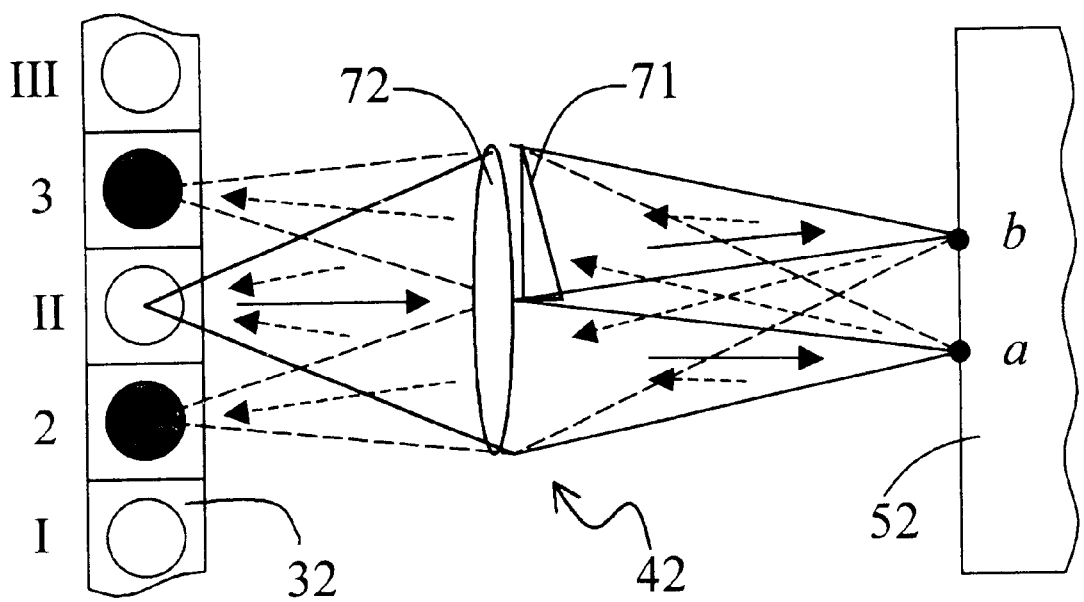
FIG. 4A is a schematic view of a first embodiment of a SABS for the confocal scanning device.
Figure 4B:
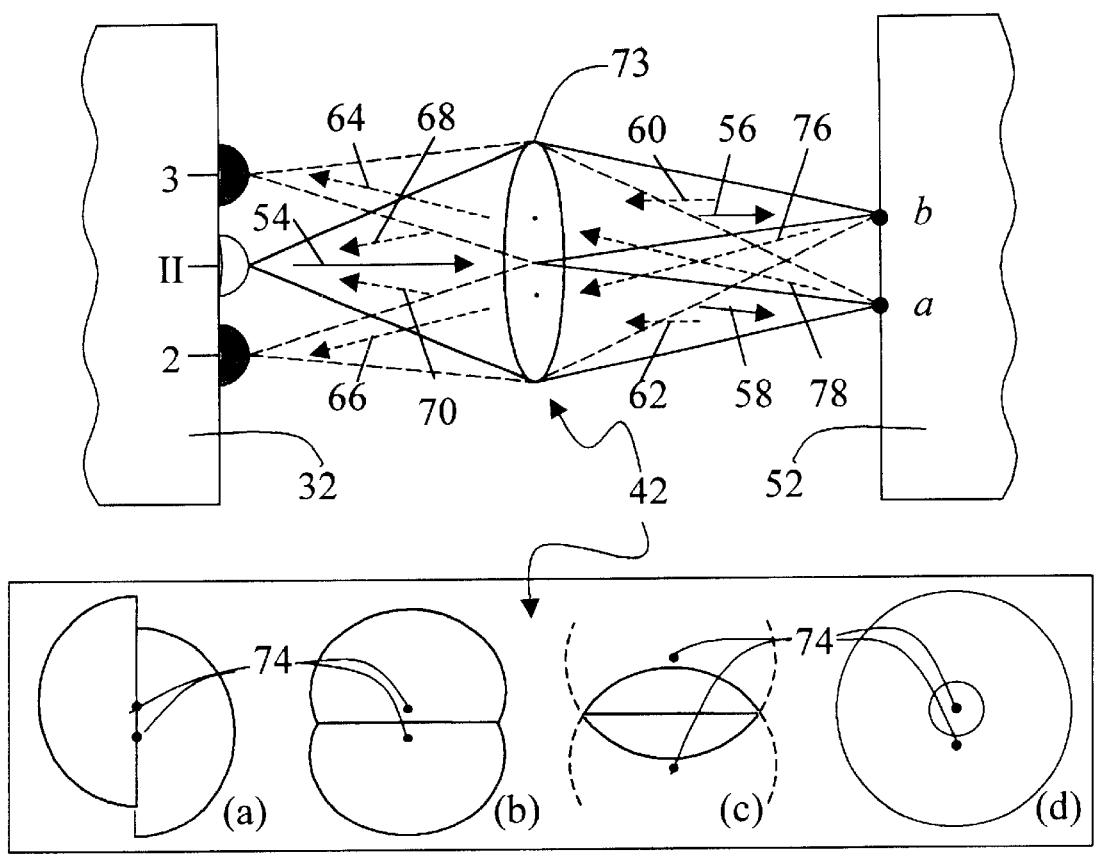
FIG. 4B is a schematic view of another embodiment of a SABS for the confocal scanning device.

FIGS. 4A and 4B

Small Angle Beam Splitter (SABS) for a Confocal Laser Scanning Device

An SABS for a confocal scanning device is shown in FIGS. 4A and 4B using the principles shown and described in connection with FIGS. 2A and 2B, and 3A, 3B and 3C.

In FIG. 4A, the small angular displacement needed for the light shift from the laser to the adjacent detector is provided by a thin prism 71 installed immediately adjacent to objective lens 72 and overlapping the half of the pupil. A diffraction grating 71 can be used to perform the same function in this schematic as a prism.

FIG. 4B shows the more preferable embodiment based on a split lens or bilens 73. The bilens 73 consists of two parts with shifted optical centers 74 but with the same optical power. The different versions of the bilens 73 are shown in the inset box as (a), (b), (c), and (d). The purpose is to provide a function that deflects the light sufficiently that the reflected and scattered light shifts ultimately the distance between the laser and the detector. The version (d) of bilens 73 is good for the well-collimated beam of microlaser that fills only the central part of bilens 73. The beam of remitted light from the object, which is formed as a wider cone, is collected by the peripheral part of the bilens 73 and is shifted due to the shifted optical center of this part.

As shown in FIG. 4B, when microlaser "II" is activated it produces light, the rays thereof being indicated by arrow 54, and the optical system 42 with the SABS produces two sets of rays of interest 56 and 58 which illuminate spots or points "b" and "a", respectively, on the object 52 from the currently operating laser 30 identified as "II". The light from each point "b" and "a" is reflected back as shown by arrows 60 and 62, respectively, to SABS 42 and is split again as shown by arrows 64, 66, 68 and 70. Part of the light, as shown by arrows 68 and 70 meets the array plane in initial position where the laser "II" is located. Another part of the light, as shown by arrows 64 and 66 is in shifted position with the detectors. Light designated by arrow 64 impinges upon detector "3" and light designated by arrow 66 impinges upon detector "2".

Since the bilens 73 is used as the SABS in this embodiment, there are other light rays of interest. These are shown by arrow 76 which is the light coming from point "b" on the object which passes through the lower portion of bilens 73, and arrow 78 which is the light coming from point "a" on the object which passes through the upper portion of bilens 73.

The bilens 73 and the lasers and detectors are arranged so that in FIG. 4B a light ray can pass from point "a" through the upper half of bilens 73 and to detector "3" so that the ray goes through the lens at a point where there is no refraction of this beam. Also, the arrangement is provided that a light ray can pass from point "b" through the lower half of bilens 73 and to detector "2" so that the ray goes through the lens at a point where there is no refraction of this beam.

If a bilens alone were to be used, the shift would be required to be one half the distance between adjacent or coordinated lasers and detectors in the array. For example, if the laser-detector spacing is 10–20μ, the bilens shift would be required to be in the order of 5–10 μm. However, it is extremely difficult (if even possible) to make a bilens with such precision, that is, with such a small difference between the two lenses. Advantageously, this problem is solved in the present invention using a complex optical system in which bilens shift could be 1 mm and still provide the required deflection. This is based on the formulas that are set forth and explained in detail in the detailed description of FIGS. 5A, 5B and 5C.

To reduce the time for imaging acquisition in the present invention, more than one laser/detector combination on the chip can be turned on simultaneously, provided there is no cross talk between the detectors. This is in contrast to conventional confocal microscopy where it is not possible to detect multiple points simultaneously.

Figure 5A:
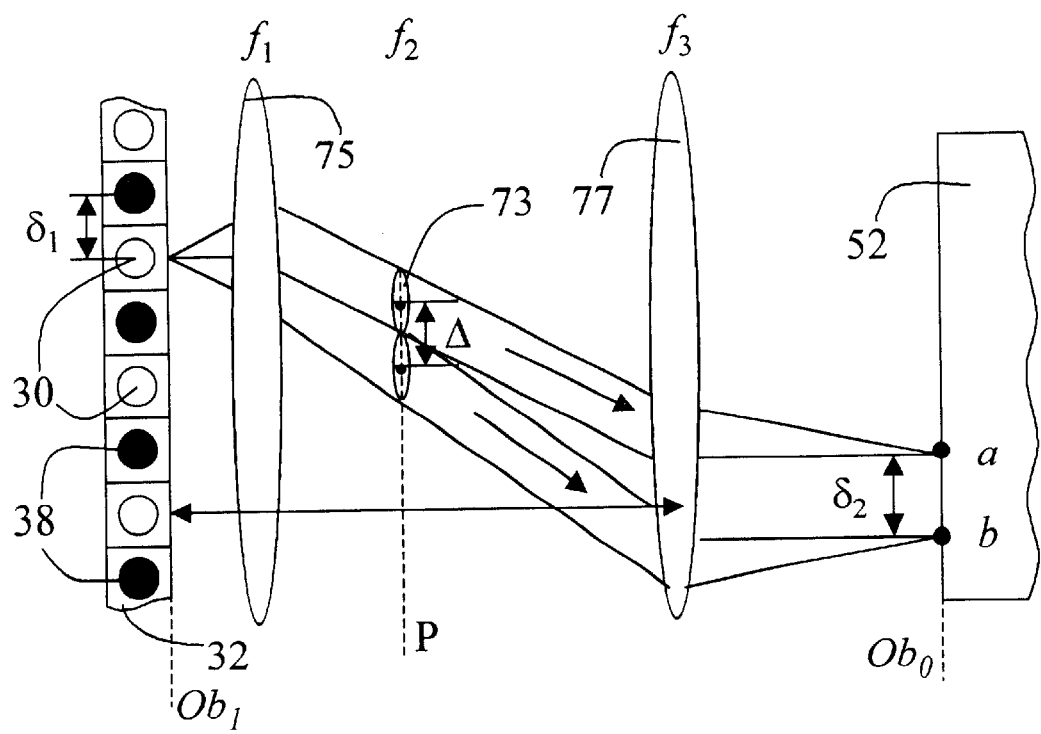
FIG. 5A is a schematic view of a confocal scanning microscope using a bilens illustrating the confocal illumination of two points on the object being viewed.
Figure 5B:
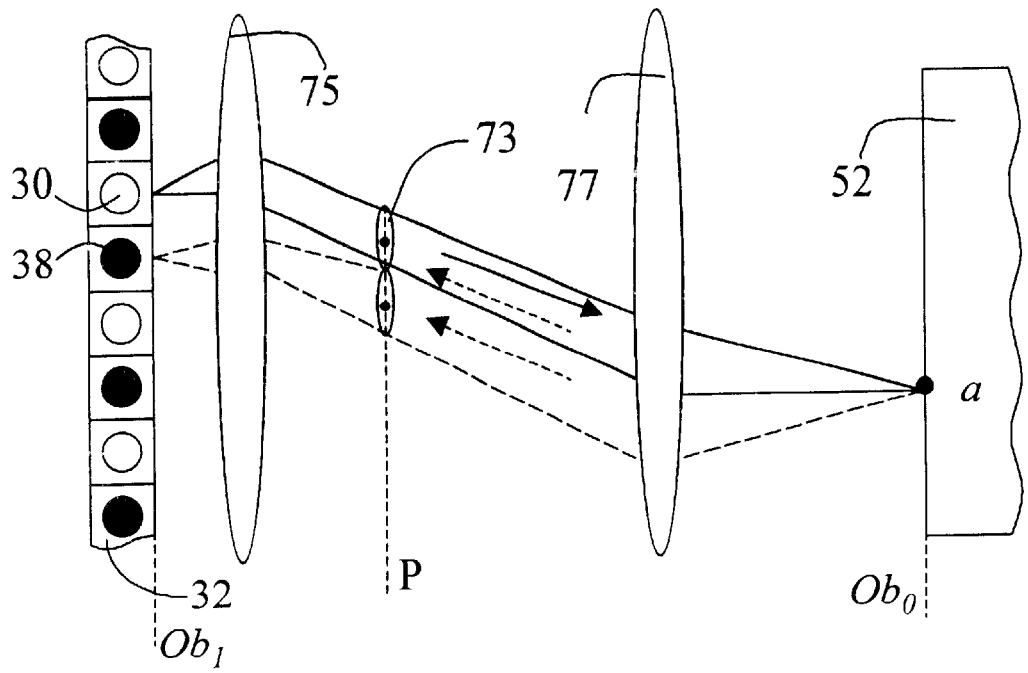
FIG. 5B is a schematic view of the microscope of FIG. 5A illustrating the confocal detection of one point on the object being viewed.
Figure 5C:
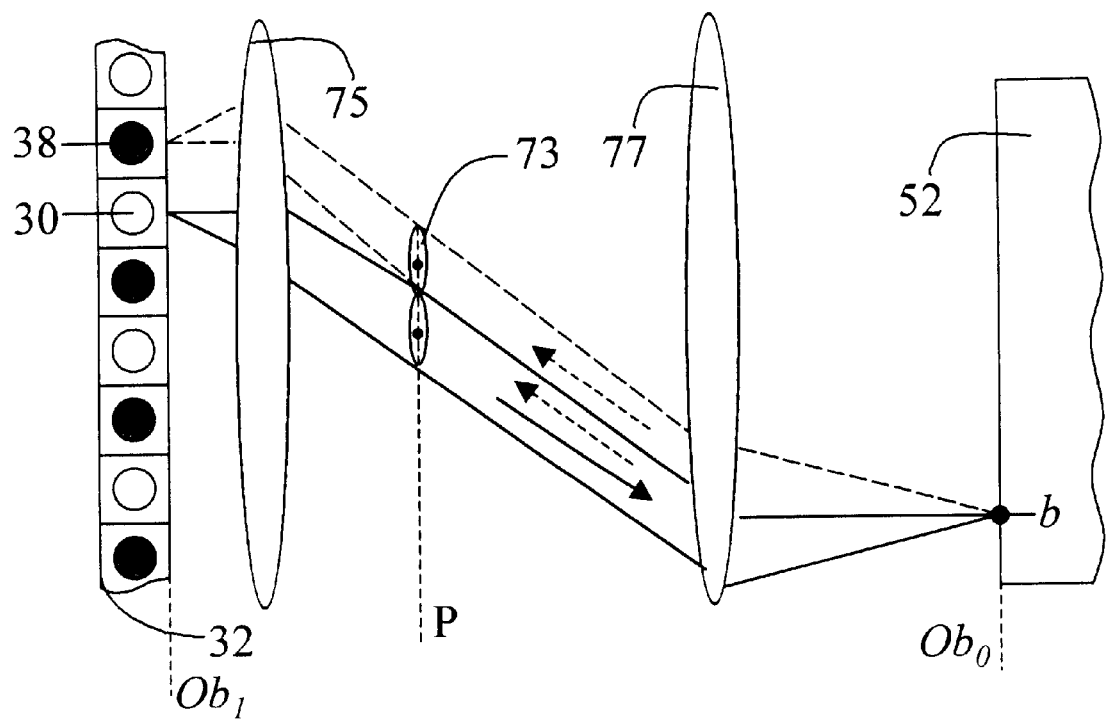
FIG. 5C is a schematic view of the microscope of FIG. 5A illustrating the confocal detection of another point on the object being viewed.

Confocal Laser Scanning Microscope—FIGS. 5A, 5B and 5C

FIGS. 5A, 5B and 5C are diagrammatic views showing a confocal laser scanning microscope (CLSM) based on a combined array 32 of microlasers 30 and detectors 38 and on bilens 73. Bilens 73 is installed in the pupil plane P of an optical system comprising two objective lenses 75 and 77. FIG. 5A demonstrates the confocal illumination of two points "a" and "b" on object 52. FIG. 5B shows the confocal detection of point "a", and FIG. 5C does so for the point "b".

FIG. 5A shows the light beams from the microlaser 30 passing through the first objective lens 75, and the beams as they enter bilens 73, and also the beams between the bilens 73 and the second objective lens 77, as well as the beams as they impinge on both points "a" and "b".

FIG. 5B shows the light beams as they leave the microlaser 30 and pass through the three lenses 75, 73, and 77, and impinge upon point "a" on the object 52, as well as the light which is reflected and remitted from point "a" back through lenses 77, 73 and 75 to impinge upon the detector 38 immediately below the just activated microlaser 30.

FIG. 5C shows the light beams as they leave the microlaser 30 and pass through the three lenses 75, 73 and 77, and impinge upon point "b" on the object 52, as well as the light that is reflected and remitted from point "b" back through lenses 77, 73 and 75 to impinge upon the detector 38 immediately above the just activated microlaser 30.

Let the focal lengths of the lenses 75, 73 and 77 be correspondingly $f_1$, $f_2$, and $f_3$. If the distance between neighboring elements of array 32 is $\delta_1$, then:

$$\Delta = \delta_1 f_1 / f_2 \quad [1]$$

$$\delta_2 = \delta_1 f_3 / f_1 \quad [2]$$

where $\Delta$ is the distance between the optical centers of bilens, $\delta_2$ is the distance between sequentially illuminated points on the object.

The first of these equations is important because it allows one to create a bilens 73 with a center shift that is significantly more than required shift of image at the array plane $Ob_1$ when the optical power of bilens 73 is much less than that of objective lens 75. This makes the creation of bilens 73 easy. On the contrary, the spatial resolution over imaged object $\delta_2$ does not depend on the focal length of the bilens according to the second equation.

Figure 6A:
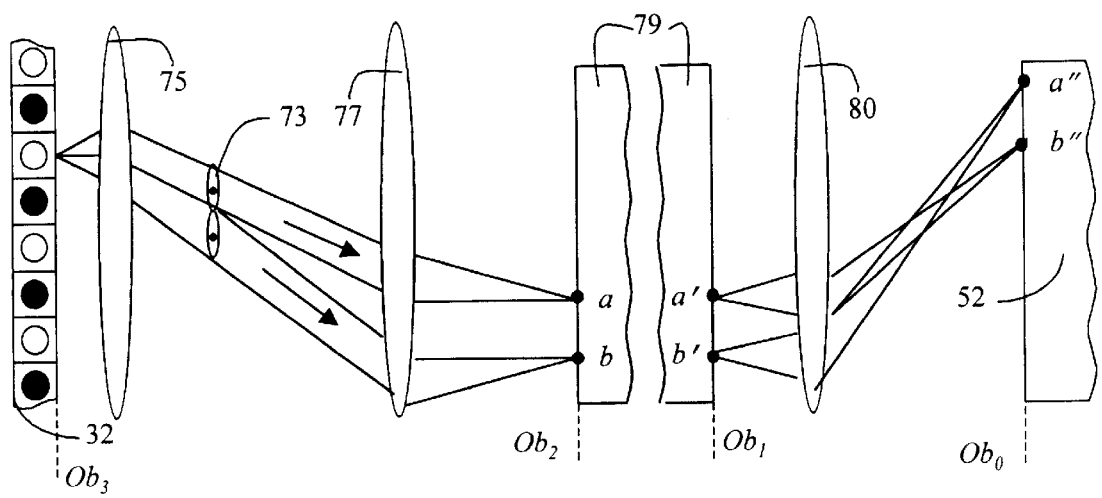
FIG. 6A is a schematic view of a confocal microscope for indirectly viewing an object.
Figure 6B:
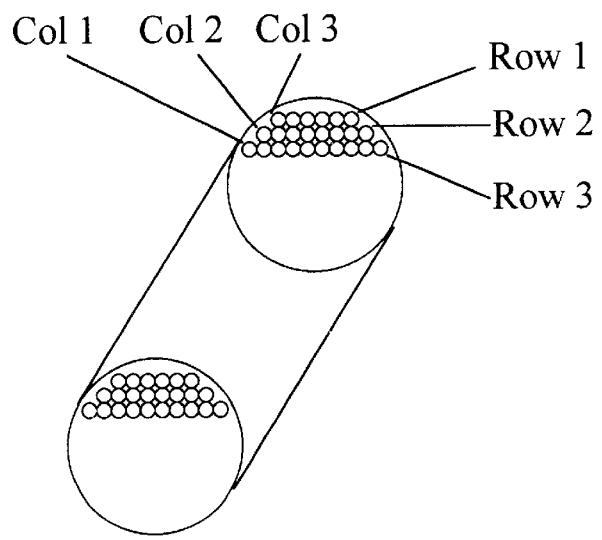
FIG. 6B is a detailed view of a bundle of fibers in a fiber optic bundle.

Confocal Scanning Device With A Remote Object—FIGS. 6A and 6B

FIG. 6A shows an embodiment of a confocal microscope for the examination of not directly accessible object 52. It includes, additionally, fiber bundle 79 for the transfer of both light from microlasers and light returned from the object. The lens 80 provides the optical conjugation of the object plane $OB_0$ and distal end $OB_1$ of fiber bundle 79. The proximal end of fiber bundle $OB_2$ is placed in the same position as the object 52 in FIG. 5A.

Therefore, during the work of each laser, the image of a pair of simultaneously illuminated spots "a" and "b" on the proximal end of the fiber bundle 79 is transferred from the distal end $Ob_1$ (points "a'" and "b'") and is projected onto the surface of object plane $Ob_0$ (points "a''" and "b''"). The light reflected, scattered or fluoresced by the spots "a''" and "b''" is focused in the points "a'" and "b'" and transferred into the points "a" and "b". Since each fiber is aligned with a specific laser and specific detector, only two fibers from the bundle 79 are used at a time for detection.

When fiber bundle 79 is coherent, the light after that is detected by two detectors neighboring emitting laser as shown in FIG. 5B and FIG. 5C. With coherent fibers, spacing can be a problem since there is an offset from row to row, but this can be solved by producing the chip with spacing similar to the lasers and detectors.

Coherency with respect to a fiber bundle means that the order of fiber tips at the proximal and at the distal ends of the bundle is the same. Such bundles are used for the transfer of the image from one end of the bundle to the other. In the present invention, the image of the object is obtained point by point and is then reconstructed. In this case, the detection of object points may be done in any order, possibly different from the order of their actual disposition. With this, if the correspondence between the arrangement of points and the order of their detection is known, then the reconstruction of an image from detected data is possible. Again, FIG. 6A shows the use of such a coherent fiber bundle 79.

This concept allows the use of non-coherent fiber bundles. For example, FIG. 6B shows a fiber bundle 79' that is similar to fiber bundle 79 of FIG. 6A, except that it is a non-coherent bundle 79'. Such bundles usually are not used for imaging but only for illumination of the object. They are much less expensive than coherent bundles, and this reduces the price of the fiber confocal microscope according to the present invention. The use of such a fiber bundle will require the calibration procedure for each bundle that will establish the arrangement of stored data from detectors for the construction of a correct image.

FIG. 6B shows such a non-coherent fiber bundle, which is in the shape of a "U" for illustrative purposes only so that each end of the fiber bundle can be seen aligned with the other end. With a non-coherent fiber bundle, there is a difference from the coherent fiber bundle. A few rows and columns of fibers of the bundle are shown at each end. In a coherent bundle, the fiber at Row 1, Column I at the proximal end of the bundle, is also at Row 1, Column 1 at the remote end of the bundle. However, in a non-coherent bundle, the fiber at Row 1, Column 1 at the proximal end can be located anywhere at the remote end of the bundle, for example, at Row 2, Column 3. For each fiber bundle, what may be termed the imaging scramble matrix from one end to the other end is unique and fixed. A laser array and a two-dimensional, matrix-addressable detector array will be placed on imaging plane $Ob_3$, and the object plane $OB_0$ of FIG. 6A, respectively, to determine the imaging scramble conversion matrix. By sequentially turning on the laser and recording the coordinates of detectors that detect maximum laser light, one can obtain the fiber scramble matrix. A record is made of each, and the information is placed into a computer that then interprets the information so that, when it is displayed, it is displayed as though a coherent bundle was being used.

This calibration involves noting a fiber, for example at Row 1, Column 1, which corresponds with a particular laser or detector at the proximal end (to the array), and passing a light through it and noting where the other end of the fiber is located at the proximal end (in the fiber end-view), that is noting the Row and Column. When each of the fibers has been associated with a laser and detector at the proximal end and the location of the other end of the fiber is noted at the far end, this information can be placed into a computer associated with the display device so that, when the results are displayed, the information at the far end will be coordinated with the particular lasers and detectors at the proximal end. With this, the picture shown on the display device will be an accurate representation even though a non-coherent fiber bundle has been used.

The array as shown in FIG. 2B is shown with the columns and rows aligned, but this may need to be changed, depending upon how the fibers in the bundle are aligned at the proximal end and at the remote end. For example, if the lasers and detectors are arranged as shown for the arrangement of fibers in FIG. 6B, then each fiber end will be associated with a particular microlaser or detector.

Figure 7A:
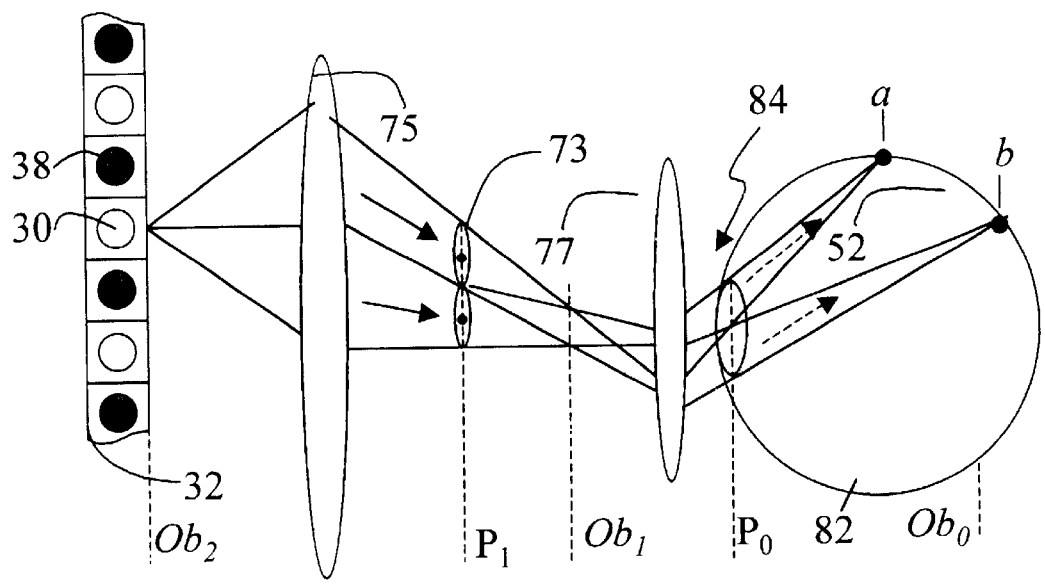
FIG. 7A is a schematic view of another embodiment of a confocal ophthalmoscope according to the present invention.
Figure 7B:
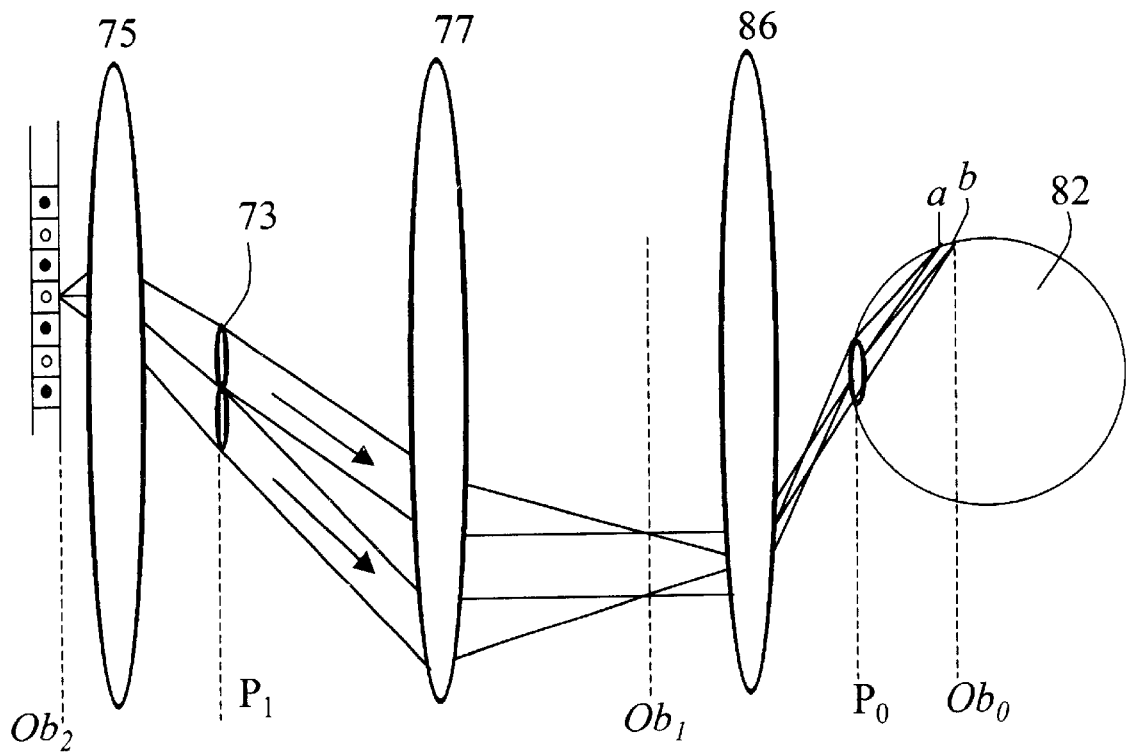
FIG. 7B is a schematic view of a further embodiment of a confocal ophthalmoscope similar to that of FIG. 7A.

Confocal Scanning Ophthalmoscope—FIGS. 7A and 7B

FIGS. 7A and 7B are diagrammatic views of the optical design of an ophthalmoscope according to the invention. The design of FIG. 7A is similar to that of FIG. 5A, but the lens 77 produces parallel light beams 84 entering the eye 82 through the pupil in the plane $P_0$. The eye focuses the parallel beams on the retina at points "a" and "b". The bilens 73 is placed at the intermediate pupil plane $P_0$. The light of each microlaser 30 produces two illuminated spots "a" and "b" on the retina. The reflected and remitted or fluoresced light is detected by two detectors 38 neighboring the currently operating laser 30. The return light path is not specifically shown in FIG. 7A. Fluoresced light is involved when a dye is used, e.g., dye injected into a patient for this purpose. Lens 77 provides the conjugation of $P_1$ and $P_0$. Lens 77 is much stronger than a person's eyeglasses and therefore with only slight adjustment can focus on points "a" and "b" for persons who wear eyeglasses to compensate for the person's own lenses not being perfect and, therefore, not focusing exactly on points "a" and "b".

Another embodiment of an ophthalmoscope is shown in FIG. 7B. Two lenses 77 and 86 are used here, instead of only one lens 77 as in FIG. 7A, for creation of intermediate pupil at the plane $P_1$ where the bilens 73 is placed. Lenses 77 and 86 form a telescopic system. For example, if a 3× magnification is desired for the telescopic system, the ratio of the focal lengths of lens 77 to lens 86 should be 3:1. This is useful in various situations, such as when a bright light is being used (or the room light is bright) wherein the iris of the eye closes down (and this could be to 1 mm). In such an event, the magnification permits easy viewing even though the amount of light entering the eye is reduced due to the closing down of the person's iris. As a comparison, when there is little light, the iris could be 4–7 mm.

The lens 86 can be changed, and one can adjust the ratio of the diameter of the bilens 73 to the pupil of the eye. The ratio of the bilens 73 to the pupil of the eye is equal to the ratio of the focal length of lens 77 to the focal length of lens 86. The lenses 77 and/or 86 can be changed to adjust the ratio of the focal lengths to provide different amounts of magnification to the telescopic system. This can also be done for the arrangement shown in FIG. 7A, but then the entire lens system must be adjusted.

Figure 8A:
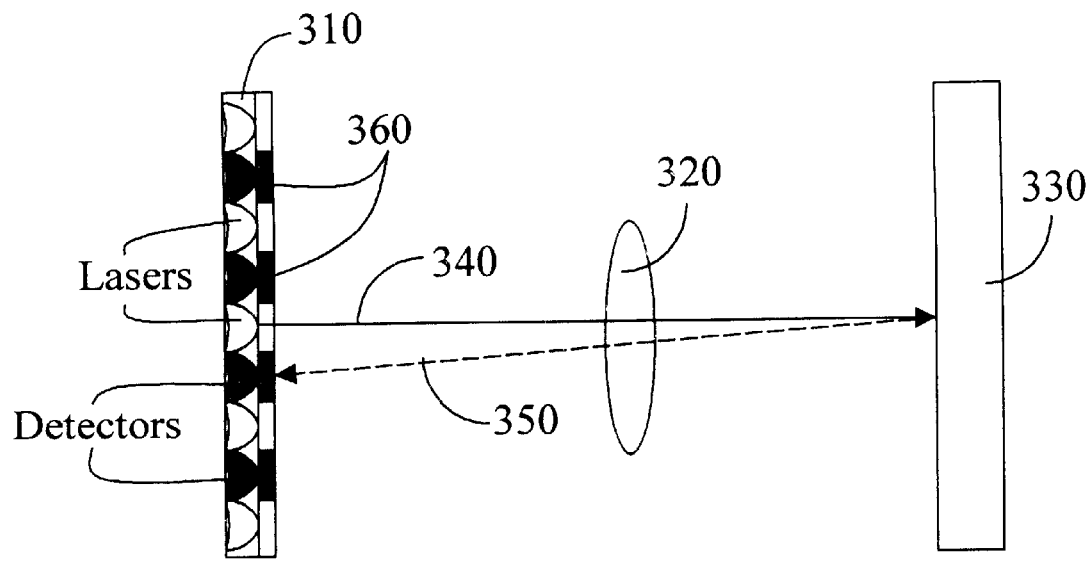
FIG. 8A is a schematic view of a confocal scanning fluorescence microscope embodying the present invention.
Figure 8B:
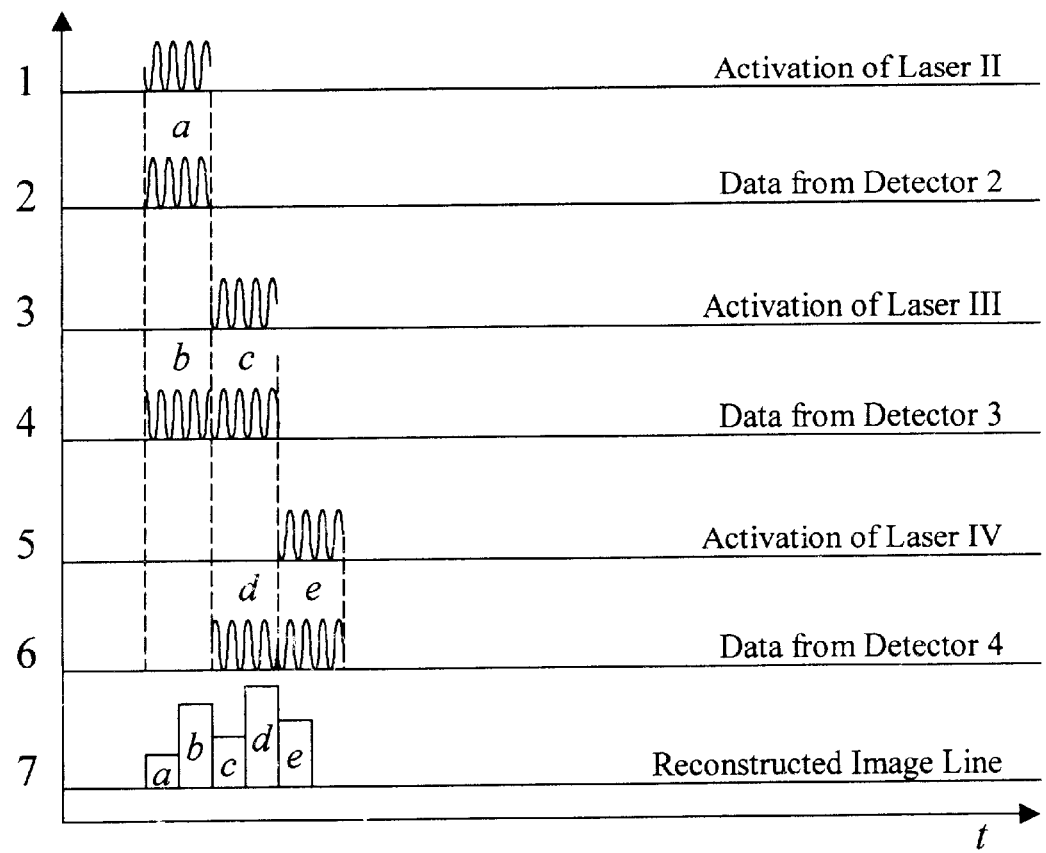
FIG. 8B is a graphical depiction of the time charts in the fluorescence lifetime mode operation of the scanning microscope device.

Measurement of Fluorescence Intensity and Lifetime—FIGS. 8A, 8B

Fluorescent light is spectrally shifted in relation to illumination light. Referring to FIG. 2B, detectors 38 in a combined laser/detector array 32 should be sensitive to light with a longer wavelength than the light emitted by microlasers 30 to detect fluorescence. In this case, detectors can not have the same resonance cavity as microlasers. The light reflected from the object should not be detected in order to increase the contrast of fluorescence image because the reflected light from the image will reduce contrast. For this reason, the rows of detectors 38 on the substrate 40 should be covered with a long-pass optical filter, which will cut-off the reflected light and will be transparent to fluorescent light. The making of such small optical filters is not a problem;

they are widely used in the creation of color CCD chips. The use of a modified chip according to the description above permits the detection of the distribution of fluorescence intensity over the object in all of the above described embodiments, when the intensity of each microlaser is steady during its operating period.

FIG. 8A shows a confocal scanning fluorescent microscope having a laser/detector array 310 in which the lasers emit light shown by arrow 340 that passes through the optical system 320 of one of the types disclosed herein thereby to impinge on a point on object 330, which in this case could be a tissue sample. The light is reflected from this point and passes through optical system 320 as shown by arrow 350 and impinges on a detector in the array 310. FIG. 8A shows (on the left side thereof) the two-dimensional laser/detector array 310 having lasers and detectors. The detectors are covered by a spectral filter 360 that allows the fluorescent light to reach the detectors while blocking the normal laser light from impinging on the detectors. The fluorophore of tissue 330 is excited by the laser light 340 via lens system 320, and the emitted fluorescent light therefrom is detected by detectors on the laser/detector array 310. By sequencing the turning on of laser/detector pairs, the confocal fluorescence imaging can be detected.

The life-time of fluorescence provides important information about the chemical composition of an object. Some substances, like oxygen in liquid media, shorten the life-time depending on their concentration. Therefore, the life-time image of an object corresponds to the distribution of the substance that quenches the detected fluorescence of specific fluorophores. The application of phase method of life-time measurement [J. Lakowicz. "Principles of Fluorescence Spectroscopy." New York 1973] to the invention allows one to obtain the life-time image of an object. The confocal imaging of the lifetime will provide information about the tissue chemical compositions and dynamic behavior of the tissue cell.

The phase method is a measurement of the time delay between fluorophores' fluorescence and excitation. When the period of modulation is close to the life-time of fluorescence, the phase shift between behaviors of excitation light and fluorescence is well-distinct and proportionate to the lifetime.

The principle of construction of a life-time image is shown in FIG. 8B, which is similar to FIG. 3C referring to the construction of the intensity of an image. The distinction of FIG. 8B from FIG. 3C is in the sine wave variation of microlaser intensity. Referring to FIG. 2A, the laser/detector scan drive 36 can provide this variation by modulation of microlaser current. The frequency of such modulation can be in the GHz range. The corresponding period of modulation is close to the life-time of fluorescence, about several nano-seconds. Therefore, the number of cycles during the working interval of each laser can be high enough for measurement of the phase shift. If the number of elements in the combined laser/detector chip corresponds to VGA resolution $640 \times 480 = 3 \times 10^5$, the working interval should be equal to 30 ms/$1.5 \times 10^5$=200 nanosecond for the real-time imaging. This is a sufficiently large interval to detect the phase shift between signals with 1 GHz frequency. The image output device 46 in FIG. 2A should provide such measurement for each illuminated point on the object. Returning to FIG. 8, the reconstructed image line should reflect phase shifts between microlaser light and fluorescence detected from each point on the object.

Retardance Imaging

The measurement of birefringence is of great importance both for microscopy and for ophthalmoscopy [Hocheimer and Kues "Retinal polarization effects," Applied Optics 1982 Vol. 21, pp. 3811–3818]. This phenomenon reflects the presence of anisotropic structures in objects, like microtubule polymers in cells and optical nerve fibers in the retina.

Polarized scanning confocal devices according to the present invention should contain the array of microlasers 30 in FIG. 2B emitting linear polarized light. This can be provided either by making a special form of their cavity or by placing polarizing filters on the rows of microlasers. The detectors 38 of the same substrate 40 should detect only the light, polarizing in direction, that is perpendicular to the laser light. This can be provided by the location of corresponding polarizers on the rows of detectors of the substrate 40. Placing the quarter-wave plate between the substrate and other optical elements of any embodiment of the present invention will provide the optical schematic of circular polariscope. The intensity of the light detected by each detector 38 will depend on the retardance in the corresponding point on the object. When linear polarization is used, the tissues being examined provide another type of polarization back to the detectors, and this permits analysis of the tissue characteristics.

The commercial potential for a polarized confocal scanning microscope is difficult to predict at this time. For the cell biologist, this will be an enormously welcome tool to study anisotropy in biological material both in fixed as well as living specimens. Since the imaging could be done in "real time" (in at least video rates (30 frames/second) or better), there is the possibility there could be image changes in anisotropy during physiological processes such as signal transduction events, protein-protein interactions, DNA-protein interactions, and the like in living cells. It also can be used to monitor the optical tweezers for measuring the force required to separate antigen-antibody bonds. [Kreistan Helmerson et al., "Optical tweezers-based immunosensor detects femtomolar concentrations of antigens," *Clinical Chemistry* 43:2, pp. 379–383 (1997)].

Figure 9A:
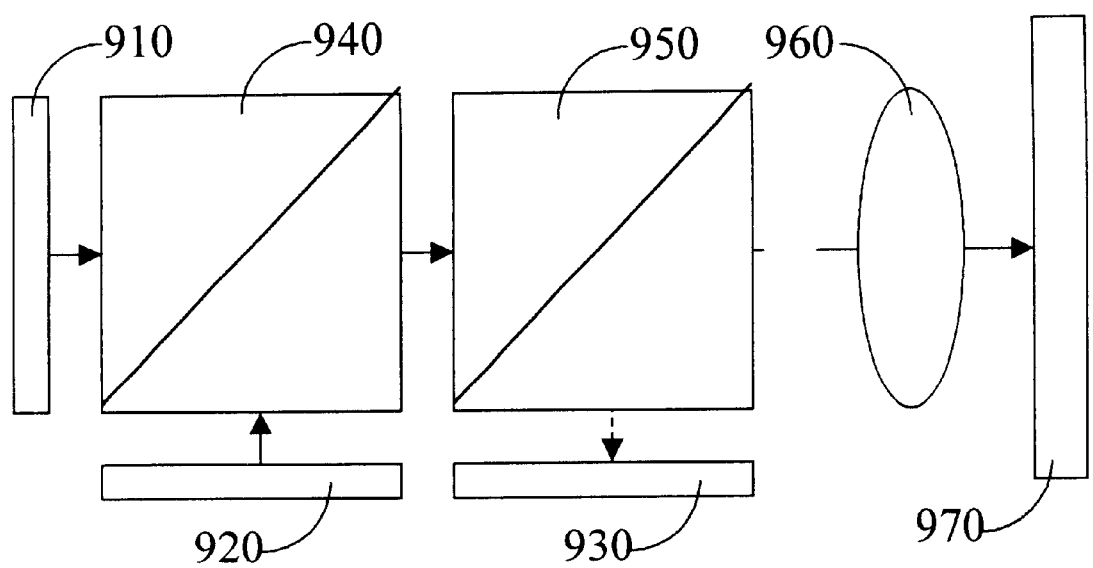
FIG. 9A is a schematic view of a two-photon fluorescence confocal microscope according to the present invention.
Figure 9B:
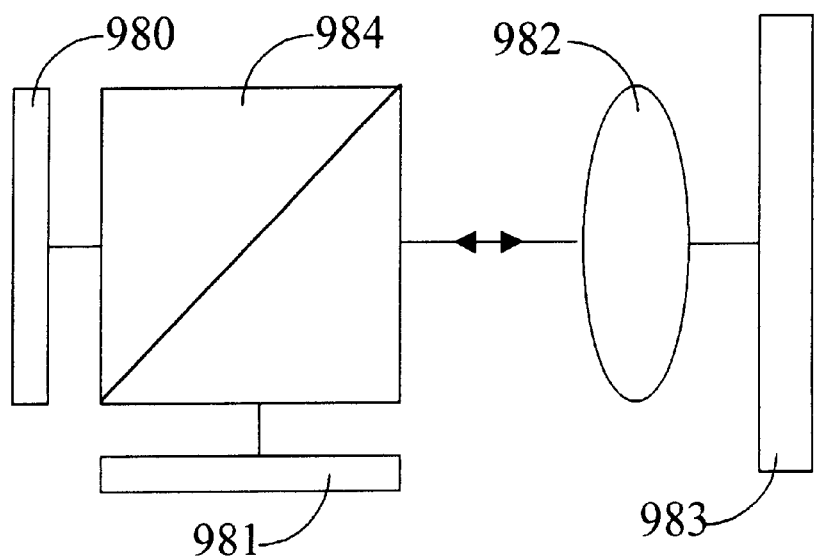
FIG. 9B is a schematic view of another type of two-photon fluorescence confocal microscope.

Two-Photon Scanning Fluorescence Microscope—
FIGS. 9A and 9B

The two-photon scanning fluorescence microscope was developed (U.S. Pat. No. 5,034,613) to reduce the problem, among others, associated with the photobleaching of fluorophores in the target material from constant exposure to light. The microscope apparatus is very similar to a confocal microscope, but instead of exciting fluorescence with single photons of short wavelength light, the same fluorescence is excited by packs of two or more photons of long-wavelength light. The difficulty is that the two-photons must arrive nearly simultaneously to impart enough energy onto the target material to create fluorescence. The two-photon wavelength is usually in the near- or mid-infrared range with femto-second pulses.

One advantage of the technique is that fluorescence occurs only in the focal volume, the three-dimensional area where the laser beam is focused and where the power density is high enough to excite fluorescence. The optical sectioning can be performed by excitation alone. The two-photon microscope can penetrate deeper into tissue because its longer excitation wavelengths scatter less and the absence of the out-of-focus photodamage allows for higher laser powers. This feature provides depth of field resolution comparable to that produced by confocal scanning microscopes, allows construction of images by collecting two-photon excited fluorescence from each point in the scanned objects while still satisfying the requirement for very high excitation intensity obtained by focusing the laser beam, and by pulse time compressing the beam.

As shown in FIG. 9A, such a device is obtained, with proper electronic circuits modifications, by simultaneously emitting two-photons, one each, from two laser arrays 910 and 920, combined by a beamsplitter 940, to the tissue 970 via a lens system 960. The two-photon induced fluorescence is detected by a detector array or CCD 930 via a dichroic mirror 950 that reflects the fluorescence and transmits the excitation light. By sequentially exciting the lasers on the arrays on and off, fluorescence imaging may be obtained.

FIG. 9B is another design of the two-photon confocal fluorescence imaging. Laser/detector arrays 980 and 981 have spectral filters. In this embodiment, the two laser beams (from 980 and 981) combined by a beamsplitter 984 illuminate points on the tissue 983 via lens system 982. This is done by having the combined laser/detector arrays 980 and 981 so that the excitation to provide the photons continues to be performed by two separate laser arrays, as in FIG. 9A, but the fluorescence from object 983 then passes directly through optical system 984. The fluorescence light will be detected by the corresponding two detectors on the arrays 980 and 981 respectively. Compared to FIG. 9A, a dichroic mirror is eliminated in this embodiment as is a separate detector array (separate from the laser array). Less light intensity is lost.

Figure 10A:
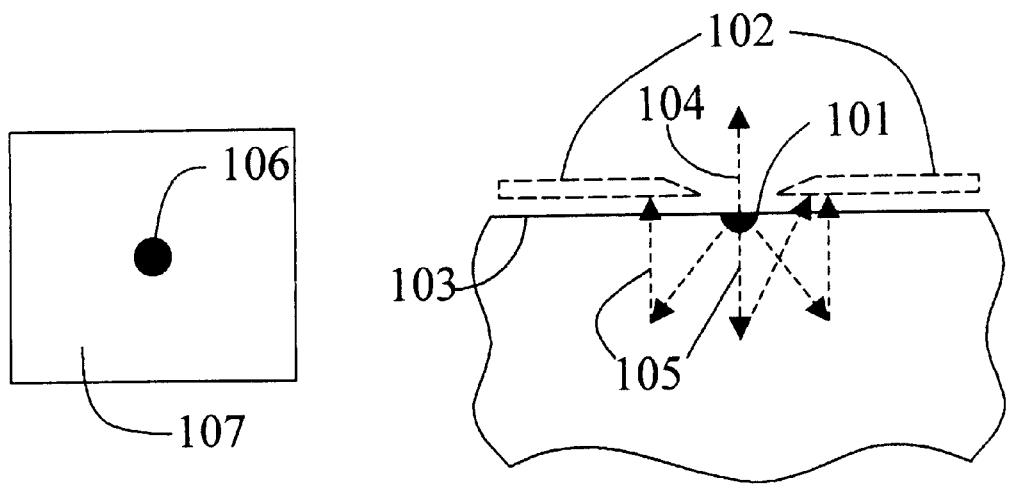
FIG. 10A is a schematic view of confocal imaging in direct pin-hole mode.
Figure 10B:
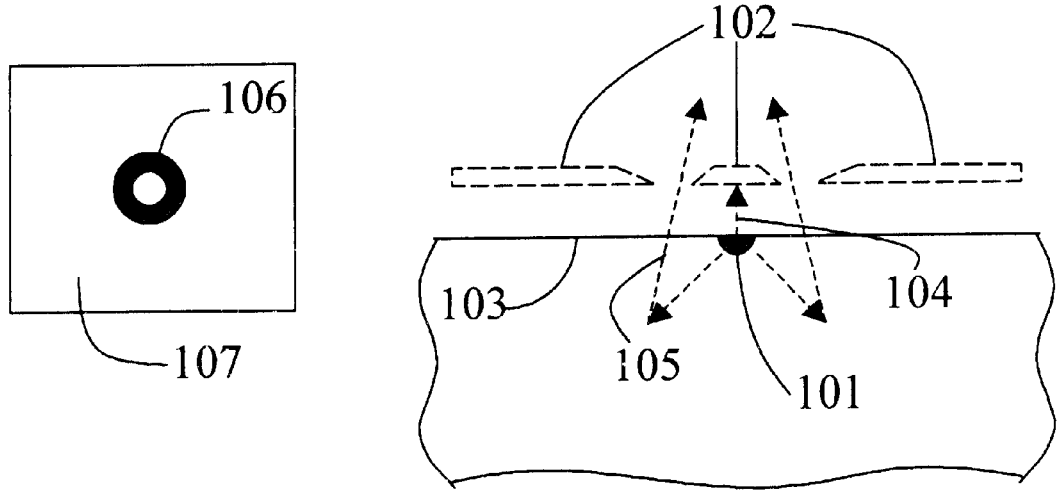
FIG. 10B is a schematic view of confocal imaging in indirect pin-hole mode.
Figure 11:
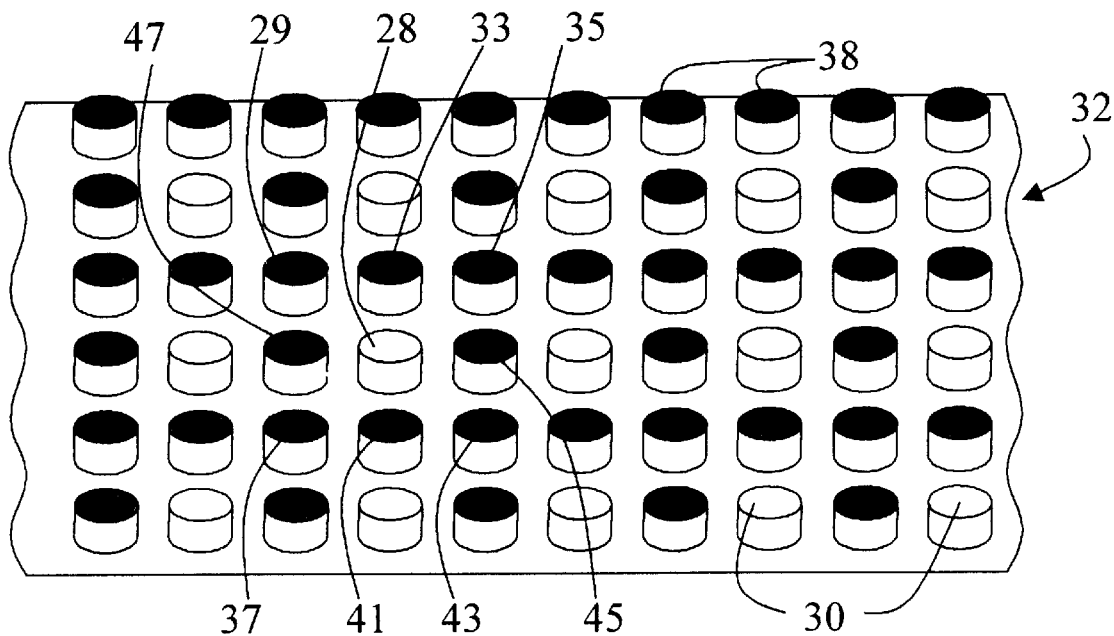
FIG. 11 is a pictorial view of a laser/detector array arranged for the indirect mode.

Indirect Scanning—Mode of Imaging—FIGS. 10A, 10B and 11

The present invention can be used not only in the confocal mode of imaging, but in the indirect mode also. The difference between these modes is explained in FIGS. 10A and 10B, shown for illustration purposes only, since the present invention does not use the type of apertures shown in these figures. The currently illuminated spot 101 on the object plane 103 is shown in these figures. The shape of detector aperture stop 102 in the same plane 103 determines which portion of the light remitted from the object will be detected.

In the confocal mode of imaging according to FIG. 10A, only the light 104 remitted directly from illuminated area 101 will be detected. The detector 106 in the image plane 107 is placed only within the boundary of the image of the illuminated spot 101. In the confocal scanning microscope of the present invention, the direct mode imaging can be seen to be achieved, for example, by turning on the laser 31 of FIG. 2B and the neighboring detector 39.

Referring to FIG. 10B, the light 104 directly remitted from the illuminated area 101 is not detected because the detector 106 in the image plane 107 has a ring-like shape surrounding the area where the image of spot 101 would be located if the aperture 102 did not have the central circular area that blocks the direct light. In this mode, only the multiple-scattered light 105 can be detected. Generally speaking, the indirect mode of scanning imaging is realized when only non-illuminated parts of the object are imaged.

The intensity of multiple-scattered light is affected by the absorption of examined tissue significantly more than that of reflected light. That perhaps is the reason its detection is found to be useful in eye examination [Webb et al., "Confocal Scanning Laser Ophthalmoscope". *Applied Optics* 1987, Vol. 26, No. 8, pp. 1492–1499] and cancer detection [Mourant et al. "Spectroscopic diagnosis of bladder cancer with elastic light scattering." *Lasers in Surgery and Medicine* 1995, Vol. 17, pp. 350–357].

According to the present invention, the indirect mode of imaging can be realized in the embodiments of FIGS. 3–7 without using bilens 73 and with another way of signal processing than described in FIG. 3C. Because of the absence of the bilens 73, only one spot of the object will be illuminated during the working period of each laser 30 in FIG. 2B, and the image of this spot will not be shifted in the plane of laser/detector array 32. Therefore, the directly reflected light will be placed onto the area occupied by the laser and will not be detected. The summary signal of six detectors neighboring to the working laser (3 above and 3 below) will represent the average level of the light that is multiple-scattered about a currently illuminated spot. The sequence of such summary signals, in accordance with the sequence of working lasers, will construct the image of the object in indirect mode.

For example, in FIG. 2B, when a specific microlaser, such as microlaser 28, is illuminated, the six neighboring detectors 29, 33, 35, 37, 41 and 43 receive the multiple-scattered light from the currently illuminated spot. If these detectors are arranged to be activated at the same time and coordinated with the illumination from microlaser 28, then an image in indirect mode can be constructed and viewed on a suitable display as described previously. While the indirect mode may possibly be used in this manner, the preferred manner of accomplishing this is described below.

The design of laser/detector array may be changed specifically for the indirect mode of imaging to obtain the best results. FIG. 11 shows the design of an array where each laser 30 is symmetrically surrounded by eight detectors 29, 33, 35, 37, 41, 43, 45 and 47, working simultaneously with this laser. Therefore, the level of summary signal of detected light is increased as compared to the embodiment shown in FIG. 2B, and the pattern of detected multiple-scattered light is more symmetrical for the embodiment shown in FIG. 11.

Microlasers, as well as any semiconductor laser, emit light within a much broader cone than do other kinds of lasers. For example, the typical divergence angle of a microlaser beam is about 20°. This characteristic tends to create problems relative to the complete utilization of light emitted by devices, such as microscopes and ophthalmoscopes, that require large optical magnification M on the path from the object to the laser/detector plane. This problem may arise, for example, when M>5.

Referring to equation number 2 above, the mentioned magnification M for the design of FIG. 5 is:

$$M=\delta_1/\delta_2=f_1/f_3 \quad [3]$$

The value of 62 is the distance between neighboring sampled points of the object. Accordingly, it determines the spatial resolution provided by the confocal device.

One can see from the last equation that, the higher the magnification, the better the sampling resolution. On the other hand, the distance between neighboring illuminated spots on the object should not be smaller than the size of each illuminated spot. The last parameter is bottom-limited by the light diffraction on the level about wavelength. Therefore, the reasonable value of M is top-limited. For the design of FIG. 5 using microlasers with a wavelength of about 1 $\mu$m (equal to the minimal reasonable value of $\delta_2$) that are arranged in a chip with a pitch $\delta_1=10$ $\mu$m, one can estimate that the maximal optical magnification is ×10 (M<10). It should be mentioned that, for M=3, the described device would provide good resolution about 3 $\mu$m on the object.

Summarizing, it can be said that the requirement about diffraction limited resolution connected with the necessary large M is not common for the proposed device. The fine-meshed structure of the laser array provides enough high spatial resolution even without magnification. As an example, the resolution of a typical conventional confocal laser ophthalmoscope is 10–20 µm on a retina that is close to the element pitch in the laser/detector array of our device.

However, if large magnification is still necessary, the optical designs of FIGS. 5 and 7 will not provide complete utilization of microlaser light. This is connected with the existence of a so-called optical invariant. Due to this phenomenon, the numerical apertures in the object and the image spaces of the light beams passing through the system are connected to the same factor M. This means that the sine of the convergence angle of the light that is focused on the object is M times more than the sine of divergence angle of the microlaser light captured by the optical system. If M is large enough, only the central part of the light cone emitted by the microlaser will pass the system and be utilized.

Figure 12:
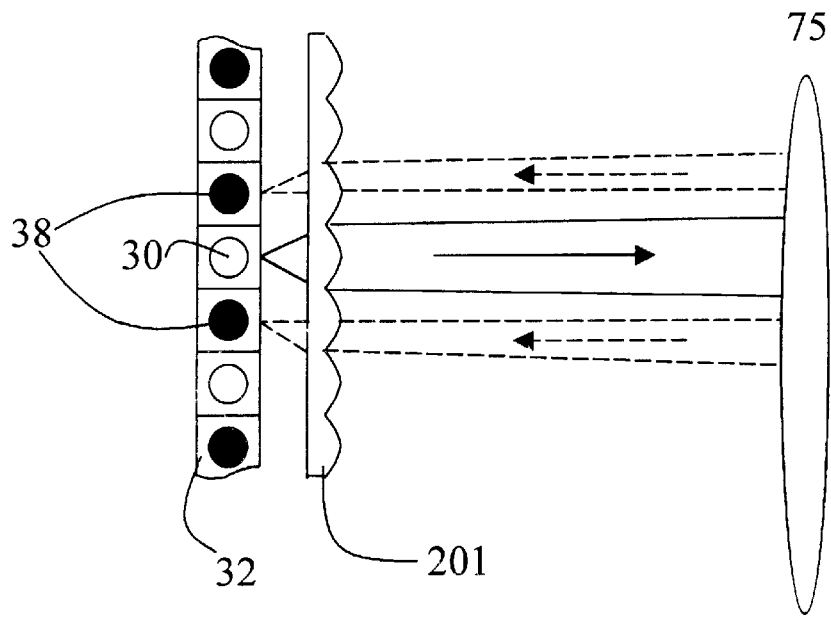
FIG. 12 is a schematic view of a further embodiment of microscope and ophthalmoscope with enhanced image brightness.

As is depicted, for example, in FIG. 12, the present invention advantageously provides a solution to this problem. There, a microlens array 201 is placed between the laser/detector array 32 and the first lens 75 of the system. The element pitch of the. microlens array 201 should match the pitch of laser/detector array 32. As used herein, the term pitch means the distance between two corresponding points on the respective element. The microlens array 201 collimates the light beam emitted by each microlaser 30 and therefore reduces its numerical aperture. Because of that, the complete light of the microlaser 30 can pass through the optical system and be focused on the object. The reflected light from the object is shifted by a bilens (not shown in FIG. 12) and focused by adjacent microlenses on the detectors 38. With this, the insertion of the microlens array in the optical design of the microscope (FIG. 5) and ophthalmoscope (FIG. 7) can significantly increase the brightness of the image and improve the sensitivity of these devices.

In light of the foregoing, it will be apparent that the present invention provides a number of advantages over devices of the prior art. Undoubtedly, further advantages beyond those specifically mentioned herein will be readily obvious both to one who has reviewed the present disclosure and to one who has an opportunity to make use of an embodiment of the present invention.

Furthermore, it will be clear that the present invention has been shown and described with reference to certain preferred embodiments that merely exemplify the broader invention revealed herein. Certainly, those skilled in the art can conceive of alternative embodiments. For instance, those with the major features of the invention in mind could craft embodiments that incorporate those major features while not incorporating all of the features included in the preferred embodiments set forth above. With the foregoing in mind, the following claims are intended to define the scope of protection to be afforded the inventor, and the claims shall be deemed to include equivalent constructions insofar as they do not depart from the spirit and scope of the present invention.

A plurality of the following claims express certain elements as a means for performing a specific function, at times without the recital of structure or material. As the law demands, these claims shall be construed to cover not only the corresponding structures and materials expressly described in the specification but also equivalents thereof.

We claim as deserving the protection of United States Letters Patent:

1. A confocal scanning device for viewing an object, the confocal scanning device comprising:

a means for illuminating the object comprising an array of microlasers;

a means for collimating light generated by the means for illuminating the object comprising a microlens array;

an optical means for directing light that is generated by the means for illuminating the object onto the object;

a means for detecting light comprising an array of detectors for detecting light from the object to which light from the means for illuminating the object has been directed; and an optical means for directing light from the object onto the means for detecting light wherein the optical means includes a bilens;

wherein the array of microlasers and the array of detectors are arranged in a single array.

2. The confocal scanning device of claim 1 wherein the microlasers are independently addressable.

3. The confocal scanning device of claim 1 wherein the array of microlasers and the array of detectors are on a single chip.

4. The confocal scanning device of claim 1 wherein a pitch of the microlens array substantially matches a pitch of the array of microlasers.

5. The confocal scanning device of claim 1 wherein the microlens array is interposed between the array of microlasers and the optical means for directing light that is generated by the array of microlasers onto the object.

6. The confocal scanning device of claim 1 wherein the optical means for directing light that is generated by the array of microlasers onto the object and the optical means for directing light from the object onto the means for detecting comprise a single optical means.

7. The confocal scanning device of claim 6 wherein there is at least one detector adjacent to each microlaser and wherein the single optical means comprises the bilens and an accompanying lens system.

8. The confocal scanning device of claim 7 wherein the accompanying lens system includes two objective lenses, and the relationship is as follows:

$$\Delta = \delta_1 f_1 / f_2$$

$$\delta_2 = \delta_1 f_3 / f_1$$

where $\Delta$ is the distance between the optical centers of the bilens, $\delta_2$ is the distance between sequentially illuminated points on the object, $\delta_1$ is the distance between neighboring elements in the array, the focal length of the bilens is $f_2$ and the focal length of the objective lens nearest the array is $f_1$, and the focal length of the objective lens furthest from the array is $f_3$.

9. The confocal scanning device of claim 1 wherein an addressing of the array of microlasers and the array of detectors is coordinated to provide information at the array of detectors significant of the object being scanned.

10. The confocal scanning device of claim 9 further comprising an imaging device means for forming an image of the object from the information detected by the array of detectors.

11. The confocal scanning device of claim 7 wherein the device is a microscope.

12. The confocal scanning device of claim 7 wherein the device is an ophthalmoscope.

13. A confocal scanning device for viewing an object wherein the confocal scanning device comprises:

a means for illuminating the object comprising an array of independently addressable microlasers;

a means for collimating light generated by the microlasers comprising a microlens array;

a means for detecting light comprising an array of independently addressable detectors for detecting light from the object to which light from the illumination means has been directed wherein the array of microlasers and the array of detectors are arranged in a single array and in a pattern constructed and arranged so that different detectors are adjacent to each microlaser whereby light from an illuminated object can be directed back to the vicinity of the illuminating microlaser and be detected by the adjacent detectors; and an optical means for directing light generated by the microlasers onto the object and for directing light from the object so illuminated onto detectors adjacent to the illuminating microlaser wherein the optical means includes a bilens.

14. The confocal scanning device of claim 13 wherein a pitch of the microlens array substantially matches a pitch of the array of means for illuminating the object.

15. The confocal scanning device of claim 13 wherein the microlens array is interposed between the array of microlasers and the optical means for directing light that is generated by the array of microlasers onto the object.

16. The confocal scanning device of claim 13 further comprising a means for controlling actuation of the independently addressable microlasers and the detectors wherein each microlaser has associated detectors and wherein the actuation is in a predetermined sequence.

17. The confocal scanning device of claim 13 wherein the device is an ophthalmoscope.

18. The confocal scanning device of claim 13 wherein the device is a microscope.

19. The confocal scanning device of claim 13 wherein the detector immediately adjacent to an activated microlaser is activated at the same time as the activated microlaser.

20. The confocal scanning device of claim 13 further comprising a bundle of fibers disposed between the single array of microlasers and detectors and the object to enable remote viewing of the object.

21. The confocal scanning device of claim 13 wherein the optical means further comprises two objective lenses, and the relationship is as follows:

$$\Delta = \delta_1 f_1 / f_2$$

$$\delta_2 = \delta_1 f_3 / f_1$$

where $\Delta$ is the distance between the optical centers of the bilens, $\delta_2$ is the distance between sequentially illuminated points on the object, $\delta_1$ is the distance between neighboring elements in the array, the focal length of the bilens is $f_2$ and the focal length of the objective lens nearest the array is $f_1$, and the focal length of the objective lens furthest from the array is $f_3$.

22. A confocal scanning imaging device for viewing an object comprising:

a means for illuminating the object comprising an array of independently addressable microlasers;

a means for collimating light generated by the microlasers comprising a microlens array;

a means for detecting light comprising an array of independently addressable detectors for detecting light from the object to which light from the means for illuminating has been directed wherein the array of microlasers and the array of detectors are arranged in a single combined array and in a pattern constructed and arranged so that different detectors are adjacent to each microlaser so that light from an illuminated object can be transmitted back to the vicinity of the illuminating microlaser and be detected by the adjacent detectors;

an optical means for directing light generated by the microlasers onto the object and for directing light from the object so illuminated onto the detectors adjacent to the illuminating microlaser wherein the optical means includes a bilens; and a means for forming an image of the object from the information detected by the means for detecting light.

23. The confocal scanning device of claim 22 wherein a pitch of the microlens array substantially matches a pitch of the array of microlasers.

24. The confocal scanning device of claim 22 wherein the microlens array is interposed between the microlasers and the optical means for directing light that is generated by the microlasers onto the object.

25. The confocal scanning device of claim 22 further comprising a bundle of fibers disposed between the single array of microlasers and detectors and the object to enable remote viewing of the object.

26. The confocal scanning device of claim 22 wherein the optical means comprises two objective lenses and wherein relationship is as follows:

$$\Delta = \delta_1 f_1 / f_2$$

$$\delta_2 = \delta_1 f_3 / f_1$$

where $\Delta$ is the distance between the optical centers of the bilens, $\delta_2$ is the distance between sequentially illuminated points on the object, $\delta_1$ is the distance between neighboring elements in the array, the focal length of the bilens is $f_2$ and the focal length of the objective lens nearest the array is $f_1$, and the focal length of the objective lens furthest from the array is $f_3$.

27. The confocal scanning device of claim 22 further comprising a second combined array of microlasers and detectors for producing two photon-induced excitations wherein the optical means combines the two laser beams by a beam splitter, a mirror, or a lens, wherein each combined array comprises a two-dimensional detector array or a charged-coupled devices (CCD) for detecting fluorescence, and wherein the combined arrays include integrated circuits for modulating at femto-seconds range.

28. A method for generating an image of an object comprising the steps of:

generating time-variant electrical excitations;

addressing the electrical excitations to microlasers in an array of independently addressable microlasers to generate non-overlapping beams of coherent light;

collimating the light with a microlens array;

directing the light onto the object wherein the directing of light is accomplished by an optical system that comprises a bilens; and detecting, in an array of detectors, light resulting from any of light scattering, light reflection, or light transmission from the object by independently addressing each detector in the array when it is to detect reflected and remitted light;

wherein the array of microlasers and the array of detectors are arranged in a single combined array.

29. The method of claim 28 wherein the array of microlasers and the array of detectors are arranged in a single array and wherein the spacing between microlasers and detectors in the combined array is less than 90 μm.

30. The method of claim 28 wherein the directing of light is accomplished by an optical system that further comprises two objective lenses and wherein the relationship is as follows:

$$\Delta = \delta_1 f_1 / f_2$$

$$\delta_2 = \delta_1 f_3 / f_1$$

where $\Delta$ is the distance between the optical centers of the bilens, $\delta_2$ is the distance between sequentially illuminated points on the object, $\delta_1$ is the distance between neighboring elements in the array, the focal length of the bilens is $f_2$ and the focal length of the objective lens nearest the array is $f_1$, and the focal length of the objective lens furthest from the array is $f_3$.

31. A method for generating an image of an object as defined in claim 28 wherein the step of detecting includes the detecting of fluorescence from the object.

* * * * *